(12) United States Patent
Kato et al.

(10) Patent No.: US 7,727,154 B2
(45) Date of Patent: Jun. 1, 2010

(54) ULTRASONIC DIAGNOSTIC APPARATUS

(75) Inventors: Sei Kato, Tokyo (JP); Hiroshi Hashimoto, Tokyo (JP)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 1941 days.

(21) Appl. No.: 10/704,765

(22) Filed: Nov. 10, 2003

(65) Prior Publication Data

US 2004/0097809 A1    May 20, 2004

(30) Foreign Application Priority Data

Nov. 11, 2002   (JP)   ............... 2002-326198

(51) Int. Cl.
*A61B 8/14*   (2006.01)

(52) U.S. Cl. .................................... 600/458

(58) Field of Classification Search ............... 600/447, 600/443, 458, 454, 438, 437; 424/9.5
See application file for complete search history.

(56) References Cited

U.S. PATENT DOCUMENTS

| | | | |
|---|---|---|---|
| 4,572,203 A | | 2/1986 | Feinstein |
| 5,040,537 A | | 8/1991 | Katakura |
| 5,255,683 A | | 10/1993 | Monaghan |
| 5,410,516 A | | 4/1995 | Uhlendorf et al. |
| 5,601,085 A | * | 2/1997 | Ostensen et al. ............ 600/458 |
| 5,685,310 A | | 11/1997 | Porter |
| 6,004,270 A | * | 12/1999 | Urbano et al. ............... 600/443 |
| 6,104,670 A | * | 8/2000 | Hossack et al. ................. 367/7 |
| 6,171,246 B1 | * | 1/2001 | Averkiou et al. ............. 600/458 |
| 6,193,660 B1 | * | 2/2001 | Jackson et al. .............. 600/443 |
| 6,322,505 B1 | * | 11/2001 | Hossack et al. .............. 600/437 |
| 6,340,348 B1 | * | 1/2002 | Krishnan et al. ............ 600/447 |

(Continued)

FOREIGN PATENT DOCUMENTS

JP    2000-325348    11/2000

(Continued)

OTHER PUBLICATIONS

Ultrasound Contrast Physics: McCullock. Journal of the American Society of Echocardiography vol. 13 No. 10.*

(Continued)

*Primary Examiner*—Long V Le
*Assistant Examiner*—Jacqueline Cheng
(74) *Attorney, Agent, or Firm*—Armstrong Teasdale LLP

(57) ABSTRACT

For the purpose of acquiring three-dimensional data for a contrast-enhanced image at an appropriate scan plane distance even for a different moving rate of an ultrasonic probe or for a different subject or imaged region, an ultrasonic diagnostic apparatus comprises: an image producing section for producing an image based on received data obtained from one scan plane; a correlation value calculating section for calculating a correlation value between images; a low-MI scan control section for repeatedly conducting a scan with such a low MI value as not break contrast agent until a correlation value between an initial image and a current image becomes smaller than a threshold; and a high-MI scan control section for, when the correlation value becomes smaller than the threshold, capturing one image with such a high MR value as to break contrast agent and returning control to the low-MI scan control section.

19 Claims, 20 Drawing Sheets

U.S. PATENT DOCUMENTS

| | | |
|---|---|---|
| 6,461,300 B2 | 10/2002 | Hashimoto et al. |
| 6,464,644 B2 | 10/2002 | Hashimoto |
| 6,482,159 B1 * | 11/2002 | Wiesauer et al. ............ 600/443 |
| 6,500,125 B1 * | 12/2002 | Muzilla et al. .............. 600/454 |
| 6,554,770 B1 * | 4/2003 | Sumanaweera et al. ..... 600/443 |
| 6,575,910 B2 * | 6/2003 | Averkiou et al. ............ 600/458 |
| 6,755,787 B2 * | 6/2004 | Hossack et al. ............. 600/447 |
| 6,899,681 B1 * | 5/2005 | Phillips et al. .............. 600/458 |
| 7,077,807 B2 * | 7/2006 | Torp et al. ................... 600/438 |

FOREIGN PATENT DOCUMENTS

| | | |
|---|---|---|
| JP | 2001-252268 | 9/2001 |
| JP | 2002-045360 | 2/2002 |

OTHER PUBLICATIONS

McCulloch, et al., Cardiac Sonographers' Communication, "Ultrasound Contrast Physics: A Series on Contrast Echocardiography, Article 3," Journal of the American Society of Echocardiography, Oct. 2000, pp. 959-967.

* cited by examiner

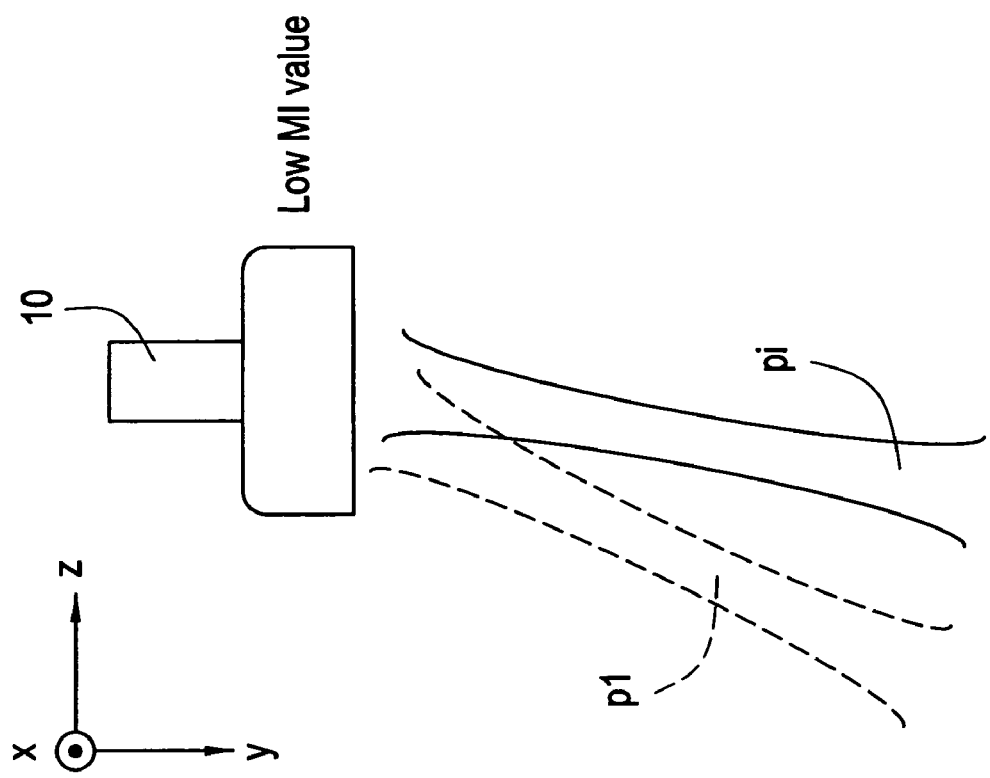
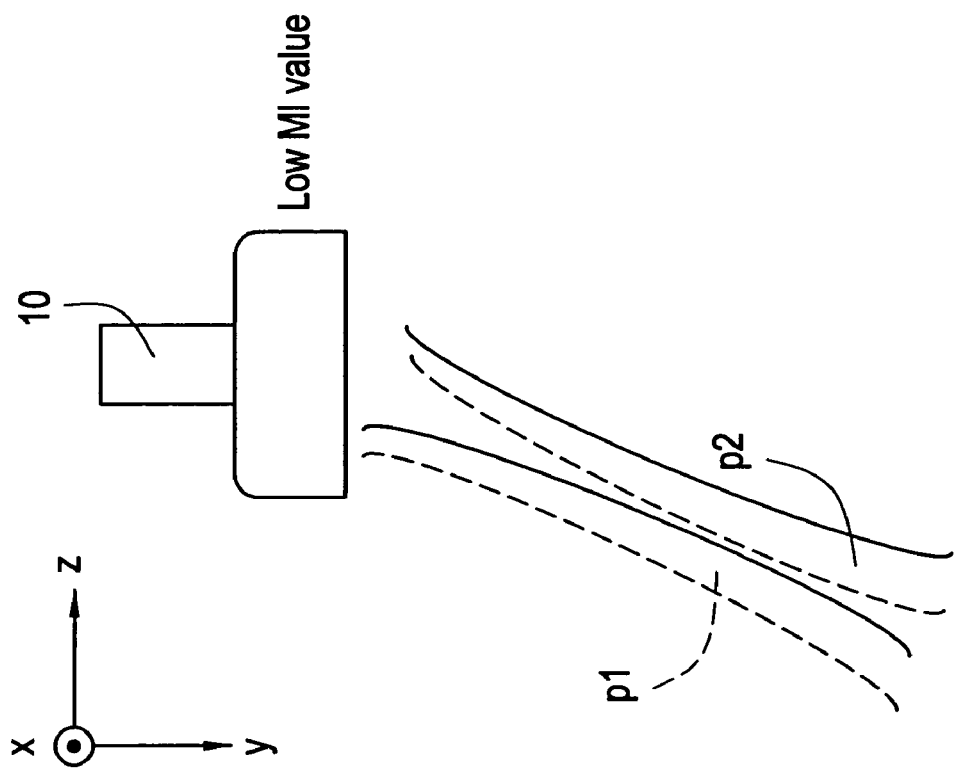

ULTRASONIC DIAGNOSTIC APPARATUS

CROSS REFERENCE TO RELATED APPLICATIONS

This application claims the benefit of Japanese Application No. 2002-326198 filed Nov. 11, 2002.

BACKGROUND OF THE INVENTION

The present invention relates to an ultrasonic diagnostic apparatus, and more particularly to an ultrasonic diagnostic apparatus that can acquire three-dimensional data for a contrast-enhanced image at an appropriate scan plane distance.

A conventional ultrasonic diagnostic apparatus captures a contrast-enhanced image by alternately conducting a scan with an ultrasonic beam at such a level as not to break contrast agent and a scan with an ultrasonic beam at such a level as to break contrast agent (see Patent Document 1, for example).

Moreover, another conventional ultrasonic diagnostic apparatus acquires three-dimensional data by obtaining images at sequentially abutting scan planes while an operator is moving an ultrasonic probe in a direction orthogonal to the scan plane (see Patent Document 2, for example).

Furthermore, still another conventional ultrasonic diagnostic apparatus employs a sensor for detecting the position of an ultrasonic probe during acquisition of three-dimensional data (see Patent Document 3, for example).

[Patent Document 1]
  Japanese Patent Application Laid Open No. 2002-045360.
[Patent Document 2]
  Japanese Patent Application Laid Open No. 2000-325348.
[Patent Document 3]
  Japanese Patent Application Laid Open No. 2001-252268.

If the conventional techniques are combined, three-dimensional data for a contrast-enhanced image can be acquired.

However, since an ultrasonic beam for capturing a contrast-enhanced image is at such a level as to break contrast agent, if the distance between adjacent scan planes is too small in acquiring three-dimensional data, even contrast agent in the current scan plane is broken by a previous scan, and good three-dimensional data for a contrast-enhanced image cannot be obtained. On the other hand, if the distance between adjacent scan planes is too large in acquiring three-dimensional data, the three-dimensional data density becomes insufficient in a direction orthogonal to the scan plane, although contrast agent in the current scan plane is prevented from being broken by a previous scan.

In the conventional techniques, it is difficult to use an appropriate scan plane distance in acquiring three-dimensional data for a contrast-enhanced image.

SUMMARY OF THE INVENTION

It is therefore an object of the present invention to provide an ultrasonic diagnostic apparatus that can acquire three-dimensional data for a contrast-enhanced image at an appropriate scan plane distance.

In its first aspect, the present invention provides an ultrasonic diagnostic apparatus characterized in comprising: an ultrasonic probe; transmitting/receiving means for driving said ultrasonic probe to scan the inside of a subject in a planar manner with an ultrasonic beam; image producing means for producing an image based on received data obtained from one scan plane; correlation value calculating means for calculating a correlation value between images; monitoring scan control means for repeatedly conducting a scan with an ultrasonic beam at such a level as not to break contrast agent until a correlation value between an initial image and a current image becomes smaller than a threshold; and imaging scan control means for, when the correlation value becomes smaller than the threshold, capturing one image with an ultrasonic beam at such a level as to break contrast agent and returning control to said monitoring scan control means.

In this configuration, the "initial image" is the first image that is acquired after control has been passed to the monitoring scan control means. That is, when control is returned from the imaging scan control means to the monitoring scan control means, the initial image is the first image that is acquired thereafter.

In the ultrasonic diagnostic apparatus of the first aspect, when the operator moves an ultrasonic probe in a direction orthogonal to the scan plane at a relatively slow rate, a scan is conducted with an ultrasonic beam at such a level as not to break contrast agent, because the correlation value between images is larger than a threshold while the distance from the initial scan plane is too small. Therefore, the contrast agent is prevented from being broken. When the distance from the initial scan plane reaches an appropriate value and the correlation value between images becomes smaller than the threshold, a scan is conducted with an ultrasonic beam at such a level as to break contrast agent. Thus, three-dimensional data for a contrast-enhanced image can be acquired at an appropriate scan plane distance even for a different moving rate of the ultrasonic probe or for a different subject or imaged region.

Moreover, the scan plane distance (i.e., the three-dimensional data density in a direction orthogonal to the scan plane) can be adjusted by modifying the threshold.

In its second aspect, the present invention provides the ultrasonic diagnostic apparatus having the aforementioned configuration, characterized in that: the apparatus comprises imaging scan time interval acquisition means for acquiring a time interval at which said imaging scan control means conducts image capture; and after one acquisition of the time interval, said imaging scan control means conducts image capture with an ultrasonic beam at such a level as to break contrast agent at said time interval without returning control to said monitoring scan control means.

In the ultrasonic diagnostic apparatus of the second aspect, after a time interval has been acquired once, image capture is conducted not with an ultrasonic beam at such a level as not to break contrast agent but with an ultrasonic beam at such a level as to break contrast agent at the acquired time interval; and therefore, calculation of a correlation value is not constantly needed, thereby simplifying processing.

In its third aspect, the present invention provides the ultrasonic diagnostic apparatus having the aforementioned configuration, characterized in that: said imaging scan control means returns control to said monitoring scan control means after conducting image capture with an ultrasonic beam at such a level as to break contrast agent at said time interval for $M$ ($\geq 1$) times without returning control to said monitoring scan control means.

In the ultrasonic diagnostic apparatus of the third aspect, the process goes back to processing for conducting image capture with an ultrasonic beam at such a level as not to break contrast agent and calculating a correlation value after conducting image capture with an ultrasonic beam at such a level as to break contrast agent for M times; and therefore, the time interval may be properly corrected in the course of acquisition of three-dimensional data.

In its fourth aspect, the present invention provides the ultrasonic diagnostic apparatus having the aforementioned configuration, characterized in that: the apparatus comprises imaging scan time interval acquisition means for acquiring a time interval at which said imaging scan control means conducts image capture; and after N ($\geqq 2$) acquisitions of the time interval, said imaging scan control means conducts image capture with an ultrasonic beam at such a level as to break contrast agent at an average or maximum of said time interval without returning control to said monitoring scan control means.

In the ultrasonic diagnostic apparatus of the fourth aspect, after a time interval has been acquired N times, image capture is conducted not with an ultrasonic beam at such a level as not to break contrast agent but with an ultrasonic beam at such a level as to break contrast agent at the average or maximum of the acquired time interval; and therefore, calculation of a correlation value is not constantly needed, thereby simplifying processing. Moreover, since the average or maximum of the time interval acquired N times is used, reliability is improved.

In its fifth aspect, the present invention provides the ultrasonic diagnostic apparatus having the aforementioned configuration, characterized in that: said imaging scan control means returns control to said monitoring scan control means after conducting image capture with an ultrasonic beam at such a level as to break contrast agent at the average or maximum of said time interval for M ($\geqq 1$) times without returning control to said monitoring scan control means.

In the ultrasonic diagnostic apparatus of the fifth aspect, the process goes back to processing for conducting image capture with an ultrasonic beam at such a level as not to break contrast agent and calculating a correlation value after conducting image capture with an ultrasonic beam at such a level as to break contrast agent for M times; and, therefore, the time interval may be properly corrected in the course of acquisition of three-dimensional data.

In its sixth aspect, the present invention provides an ultrasonic diagnostic apparatus characterized in comprising: an ultrasonic probe; ultrasonic probe position detecting means for detecting a position of said ultrasonic probe; transmitting/receiving means for driving said ultrasonic probe to repeatedly scan the inside of a subject in a planar manner with an ultrasonic beam; image producing means for producing an image based on received data obtained from one scan plane; correlation value calculating means for calculating a correlation value between images; monitoring scan control means for repeatedly conducting a scan with an ultrasonic beam at such a level as not to break contrast agent until a correlation value between an initial image and a current image becomes smaller than a threshold; imaging scan control means for, when the correlation value becomes smaller than the threshold, capturing one image with an ultrasonic beam at such a level as to break contrast agent and returning control to said monitoring scan control means; and imaging scan plane distance acquisition means for acquiring a scan plane distance at which said imaging scan control means conducts image capture by said ultrasonic probe position detecting means; wherein after acquiring a scan plane distance once, said imaging scan control means conducts image capture with an ultrasonic beam at such a level as to break contrast agent at said scan plane distance without returning control to said monitoring scan control means.

In this configuration, the "initial image" is the first image that is acquired after control has been passed to the monitoring scan control means. That is, when control is returned from the imaging scan control means to the monitoring scan control means, the initial image is the first image that is acquired thereafter.

In the ultrasonic diagnostic apparatus of the sixth aspect, when the operator moves the ultrasonic probe in a direction orthogonal to the scan plane at a relatively slow rate, a scan is conducted with an ultrasonic beam at such a level as not to break contrast agent, because the correlation value between images is larger than a threshold while the distance from the initial scan plane is too small. Therefore, the contrast agent is prevented from being broken. When the distance from the initial scan plane reaches an appropriate value and the correlation value between images becomes smaller than the threshold, a scan is conducted with an ultrasonic beam at such a level as to break contrast agent. Thus, three-dimensional data for a contrast-enhanced image can be acquired at an appropriate scan plane distance even for a different moving rate of the ultrasonic probe or for a different subject or imaged region.

After the scan plane distance has been acquired once, image capture is conducted not with an ultrasonic beam at such a level as not to break contrast agent but with an ultrasonic beam at such a level as to break contrast agent at the acquired scan plane distance; and therefore, calculation of a correlation value is not constantly needed, thereby simplifying processing.

Moreover, the scan plane distance (i.e., the three-dimensional data density in a direction orthogonal to the scan plane) can be adjusted by modifying the threshold.

In its seventh aspect, the present invention provides the ultrasonic diagnostic apparatus having the aforementioned configuration, characterized in that: said imaging scan control means returns control to said monitoring scan control means after conducting image capture with an ultrasonic beam at such a level as to break contrast agent at said scan plane distance for M ($\geqq 1$) times without returning control to said monitoring scan control means.

In the ultrasonic diagnostic apparatus of the seventh aspect, the process goes back to processing for conducting image capture with an ultrasonic beam at such a level as not to break contrast agent and calculating a correlation value after conducting image capture with an ultrasonic beam at such a level as to break contrast agent for M times; and therefore, the time interval may be properly corrected in the course of acquisition of three-dimensional data.

In its eighth aspect, the present invention provides an ultrasonic diagnostic apparatus characterized in comprising: an ultrasonic probe; ultrasonic probe position detecting means for detecting a position of said ultrasonic probe; transmitting/receiving means for driving said ultrasonic probe to repeatedly scan the inside of a subject in a planar manner with an ultrasonic beam; image producing means for producing an image based on received data obtained from one scan plane; correlation value calculating means for calculating a correlation value between images; monitoring scan control means for repeatedly conducting a scan with an ultrasonic beam at such a level as not to break contrast agent until a correlation value between an initial image and a current image becomes smaller than a threshold; imaging scan control means for, when the correlation value becomes smaller than the threshold, capturing one image with an ultrasonic beam at such a level as to break contrast agent and returning control to said monitoring scan control means; and imaging scan plane distance acquisition means for acquiring a scan plane distance at which said imaging scan control means conducts image capture by said ultrasonic probe position detecting means; wherein after N ($\geq 2$) acquisitions of the scan plane distance, said imaging scan control means conducts image capture with an ultrasonic beam at such a level as to break contrast agent at an average or maximum of said scan plane distance without returning control to said monitoring scan control means.

In this configuration, the "initial image" is the first image that is acquired after control has been passed to the monitoring scan control means. That is, when control is returned from the imaging scan control means to the monitoring scan control means, the initial image is the first image that is acquired thereafter.

In the ultrasonic diagnostic apparatus of the eighth aspect, when the operator moves the ultrasonic probe in a direction orthogonal to the scan plane at a relatively slow rate, a scan is conducted with an ultrasonic beam at such a level as not to break contrast agent, because the correlation value between images is larger than a threshold while the distance from the initial scan plane is too small. Therefore, the contrast agent is prevented from being broken. When the distance from the initial scan plane reaches an appropriate value and the correlation value between images becomes smaller than the threshold, a scan is conducted with an ultrasonic beam at such a level as to break contrast agent. Thus, three-dimensional data for a contrast-enhanced image can be acquired at an appropriate scan plane distance even for a different moving rate of the ultrasonic probe or for a different subject or imaged region.

After the scan plane distance has been acquired N times, image capture is conducted not with an ultrasonic beam at such a level as not to break contrast agent but with an ultrasonic beam at such a level as to break contrast agent at the average or maximum of the acquired scan plane distance; and therefore, calculation of a correlation value is not constantly needed, thereby simplifying processing. Moreover, since the average or maximum of the time interval acquired N times is used, reliability is improved.

Furthermore, the scan plane distance (i.e., the three-dimensional data density in a direction orthogonal to the scan plane) can be adjusted by modifying the threshold.

In its ninth aspect, the present invention provides the ultrasonic diagnostic apparatus having the aforementioned configuration, characterized in that: said imaging scan control means returns control to said monitoring scan control means after conducting image capture with an ultrasonic beam at such a level as to break contrast agent at the average or maximum of said scan plane distance for M ($\geq 1$) times without returning control to said monitoring scan control means.

In the ultrasonic diagnostic apparatus of the ninth aspect, the process goes back to processing for conducting image capture with an ultrasonic beam at such a level as not to break contrast agent and calculating a correlation value after conducting image capture with an ultrasonic beam at such a level as to break contrast agent for M times; and therefore, the time interval may be properly corrected in the course of acquisition of three-dimensional data.

In its tenth aspect, the present invention provides the ultrasonic diagnostic apparatus having the aforementioned configuration, characterized in comprising: ultrasonic probe moving means for moving said ultrasonic probe in a direction orthogonal to a scan plane at a constant rate.

In the ultrasonic diagnostic apparatus of the tenth aspect, the ultrasonic probe can be automatically moved in a direction orthogonal to the scan plane. Thus, three-dimensional data for a contrast-enhanced image can be acquired at an appropriate scan plane distance while maintaining a constant moving rate of the ultrasonic probe even for a different subject or imaged region.

In its eleventh aspect, the present invention provides an ultrasonic diagnostic apparatus characterized in comprising: a two-dimensional array ultrasonic probe; transmitting/receiving means for driving said two-dimensional array ultrasonic probe to sequentially repeat a scan of the inside of a subject in a planar manner with an ultrasonic beam and then a scan of a scan plane adjacent to the previous scan plane at a predefined distance; image producing means for producing an image based on received data obtained from one scan plane; correlation value calculating means for calculating a correlation value between images; monitoring scan control means for repeatedly conducting a scan with an ultrasonic beam at such a level as not to break contrast agent until a correlation value between an initial image and a current image becomes smaller than a threshold; and imaging scan control means for, when the correlation value becomes smaller than the threshold, capturing one image with an ultrasonic beam at such a level as to break contrast agent and returning control to said monitoring scan control means.

In this configuration, the "initial image" is the first image that is acquired after control has been passed to the monitoring scan control means. That is, when control is returned from the imaging scan control means to the monitoring scan control means, the initial image is the first image that is acquired thereafter.

In the ultrasonic diagnostic apparatus of the eleventh aspect, when image capture is repeated at a relatively small distance between scan planes, a scan is conducted with an ultrasonic beam at such a level as not to break contrast agent, because the correlation value between images is larger than a threshold while the distance from an initial scan plane is too small. Therefore, the contrast agent is prevented from being broken. When the distance from the initial scan plane reaches an appropriate value and the correlation value between images becomes smaller than the threshold, a scan is conducted with an ultrasonic beam at such a level as to break contrast agent. Thus, three-dimensional data for a contrast-enhanced image can be acquired at an appropriate scan plane distance while maintaining a constant scan plane distance even for a different subject or imaged region.

Moreover, the scan plane distance can be adjusted by modifying the threshold. That is, the three-dimensional data density in a direction orthogonal to the scan plane can be adjusted.

In its twelfth aspect, the present invention provides the ultrasonic diagnostic apparatus having the aforementioned configuration, characterized in that: the apparatus comprises imaging scan plane distance acquisition means for acquiring a scan plane distance at which said imaging scan control means conducts image capture; and after acquiring a scan plane distance once, said imaging scan control means conducts image capture with an ultrasonic beam at such a level as to break contrast agent at said scan plane distance without returning control to said monitoring scan control means.

In the ultrasonic diagnostic apparatus of the twelfth aspect, after a time interval has been acquired once, image capture is conducted not with an ultrasonic beam at such a level as not to break contrast agent but with an ultrasonic beam at such a level as to break contrast agent at the acquired scan plane distance; and therefore, calculation of a correlation value is not constantly needed, thereby simplifying processing.

In its thirteenth aspect, the present invention provides the ultrasonic diagnostic apparatus having the aforementioned configuration, characterized in that: said imaging scan control means returns control to said monitoring scan control means after conducting image capture with an ultrasonic beam at such a level as to break contrast agent at said scan plane distance for M ($\geqq 1$) times without returning control to said monitoring scan control means.

In the ultrasonic diagnostic apparatus of the thirteenth aspect, the process goes back to processing for conducting image capture with an ultrasonic beam at such a level as not to break contrast agent and calculating a correlation value after conducting image capture with an ultrasonic beam at such a level as to break contrast agent for M times; and therefore, the time interval may be properly corrected in the course of acquisition of three-dimensional data.

In its fourteenth aspect, the present invention provides the ultrasonic diagnostic apparatus having the aforementioned configuration, characterized in that: the apparatus comprises imaging scan plane distance acquisition means for acquiring a scan plane distance at which said imaging scan control means conducts image capture; and after N ($\geqq 2$) acquisitions of the scan plane distance, said imaging scan control means conducts image capture with an ultrasonic beam at such a level as to break contrast agent at an average or maximum of said scan plane distance without returning control to said monitoring scan control means.

In the ultrasonic diagnostic apparatus of the fourteenth aspect, after a time interval has been acquired N times, image capture is conducted not with an ultrasonic beam at such a level as not to break contrast agent but with an ultrasonic beam at such a level as to break contrast agent at the average or maximum of the acquired time interval; and therefore, calculation of a correlation value is not constantly needed, thereby simplifying processing. Moreover, since the average or maximum of the time interval acquired N times is used, reliability is improved.

In its fifteenth aspect, the present invention provides the ultrasonic diagnostic apparatus having the aforementioned configuration, characterized in that: said imaging scan control means returns control to said monitoring scan control means after conducting image capture with an ultrasonic beam at such a level as to break contrast agent at the average or maximum of said scan plane distance for M ($\geqq 1$) times without returning control to said monitoring scan control means.

In the ultrasonic diagnostic apparatus of the fifteenth aspect, the process goes back to processing for conducting image capture with an ultrasonic beam at such a level as not to break contrast agent and calculating a correlation value after conducting image capture with an ultrasonic beam at such a level as to break contrast agent for M times, the time interval may be properly corrected in the course of acquisition of three-dimensional data.

In its sixteenth aspect, the present invention provides the ultrasonic diagnostic apparatus having the aforementioned configuration, characterized in that: said monitoring scan control means and said imaging scan control means conduct a B-mode scan.

In the ultrasonic diagnostic apparatus of the sixteenth aspect, three-dimensional data for a B-mode contrast-enhanced image can be acquired at an appropriate scan plane distance.

In its seventeenth aspect, the present invention provides the ultrasonic diagnostic apparatus having the aforementioned configuration, characterized in that: said monitoring scan control means conducts a B-mode scan; and said imaging scan control means conducts a CFM (color flow mapping), PDI (power Doppler imaging), harmonic imaging, or contrast application scan.

In the ultrasonic diagnostic apparatus of the seventeenth aspect, three-dimensional data for a contrast-enhanced image by a CFM, PDI, harmonic imaging such as phase inversion or contrast application can be acquired at an appropriate scan plane distance.

According to the ultrasonic diagnostic apparatus of the present invention, three-dimensional data for a contrast-enhanced image can be acquired at an appropriate scan plane distance even for a different moving rate of the ultrasonic probe or for a different subject or imaged region.

Further objects and advantages of the present invention will be apparent from the following description of the preferred embodiments of the invention as illustrated in the accompanying drawings.

BRIEF DESCRIPTION OF THE DRAWINGS

FIG. 16 is an explanatory diagram showing the position of scan planes corresponding the initial image and a current image.

DETAILED DESCRIPTION OF THE INVENTION

The present invention will now be described in more detail with reference to embodiments shown in the accompanying drawings.

First Embodiment

Figure 1:
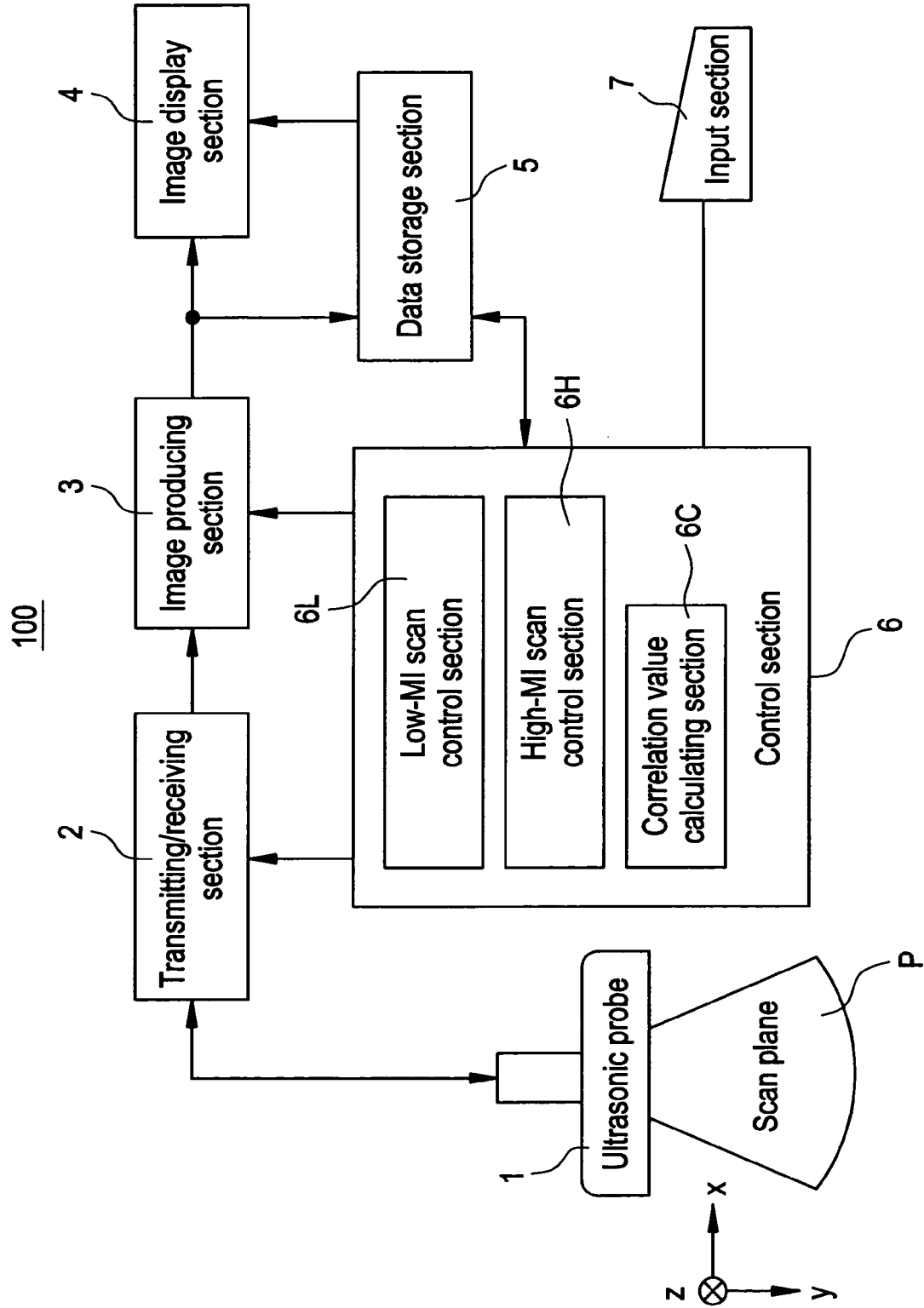
FIG. 1 is a configuration diagram showing an ultrasonic diagnostic apparatus in accordance with a First Embodiment.

FIG. 1 is a configuration diagram showing an ultrasonic diagnostic apparatus in accordance with a First Embodiment.

The ultrasonic diagnostic apparatus 100 comprises an ultrasonic probe 1, a transmitting/receiving section 2 for driving the ultrasonic probe 1 to scan the inside of a subject with an ultrasonic beam in a planar manner, an image producing section 3 for producing an image based on received data obtained from one scan plane, an image display section 4 for displaying an image, a data storage section 5 for storing images and three-dimensional data, a control section 6 for controlling the overall operation, and an input section 7 for use by an operator to specify a threshold and give instructions.

The control section 6 includes a low-MI scan control section 6L that is responsible for conducting a scan with such a low MI (mechanical index) value as not to break contrast agent, a high-MI scan control section 6H that is responsible for conducting a scan with such a high MI value as to break contrast agent, and a correlation value calculating section 6C for calculating a correlation value between images.

The MI value is a negative maximum peak sound pressure on an acoustic axis normalized by a reference sound pressure 1 Mpa.

Figure 2:
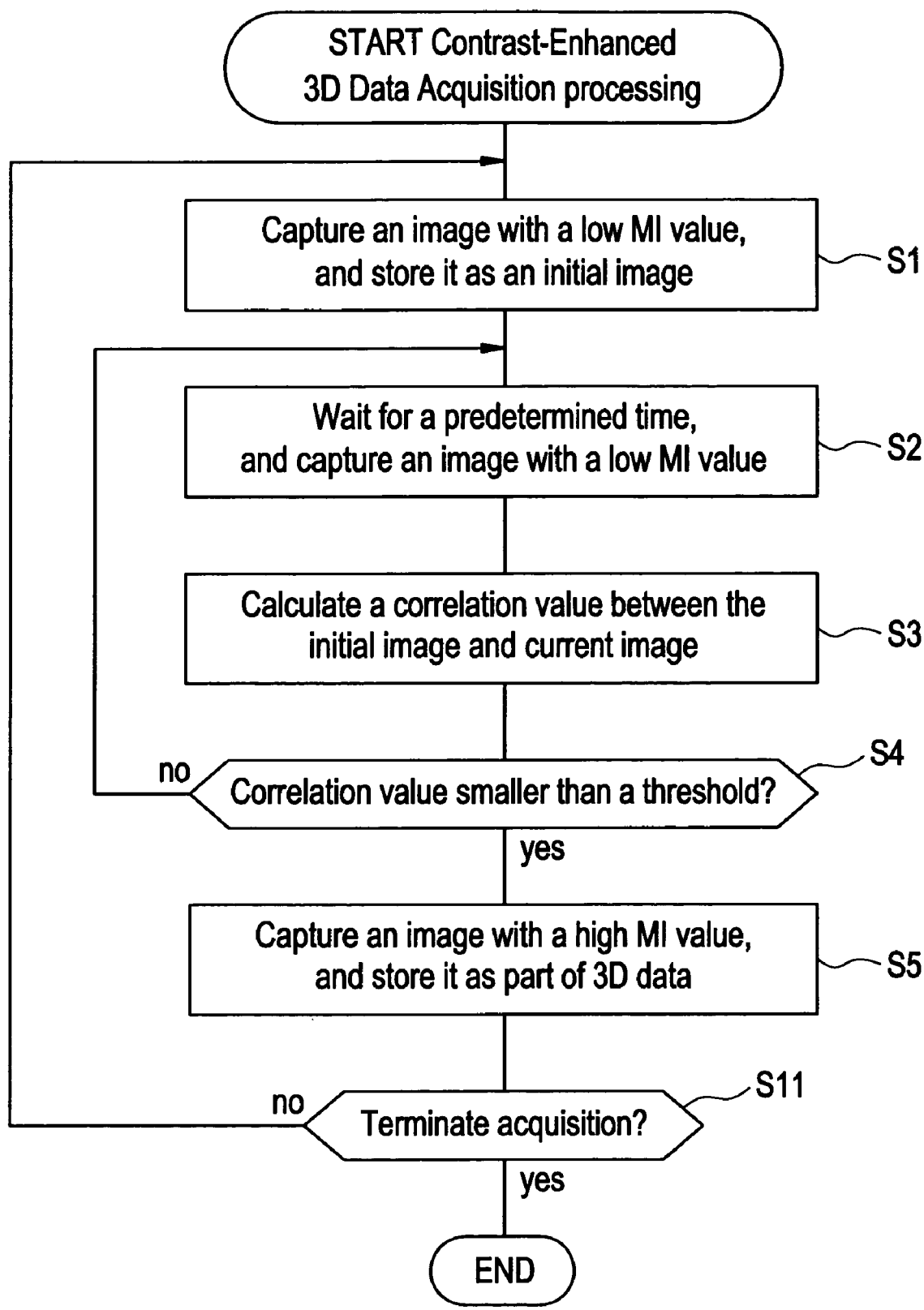
FIG. 2 is a flow chart showing contrast-enhanced three-dimensional data acquisition processing by the ultrasonic diagnostic apparatus in accordance with the First Embodiment.

FIG. 2 is a flow chart showing a first example of contrast-enhanced three-dimensional data acquisition processing by the ultrasonic diagnostic apparatus 100.

The operator injects contrast agent into a subject, puts the ultrasonic probe 1 against the subject, activates the contrast-enhanced three-dimensional data acquisition processing, and then, slowly moves the ultrasonic probe 1 in a direction (z-direction) orthogonal to its scan plane (x-y plane).

At Step S1, the low-MI scan control section 6L conducts a B-mode scan with such a low MI value as not to break contrast agent, the image producing section 3 produces a B-mode image, and the data storage section 5 stores the B-mode image as an initial image.

Figure 3:
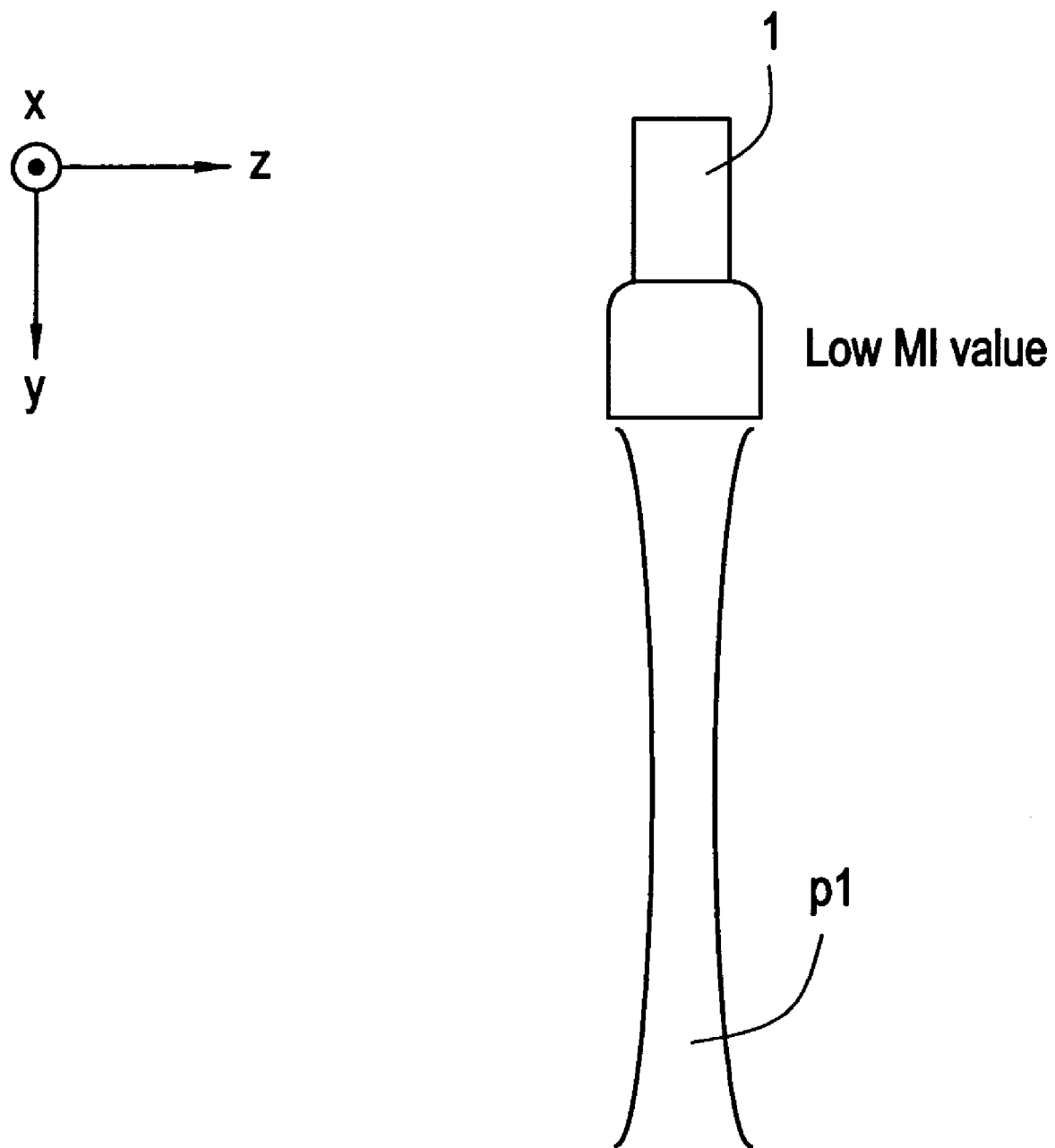
FIG. 3 is an explanatory diagram showing the position of a scan plane corresponding an initial image.

FIG. 3 shows the position of a scan plane p1 corresponding to the initial image.

At Step S2, the low-MI scan control section 6L waits for a predetermined time, conducts a B-mode scan with such a low MI value as not to break contrast agent, the image producing section 3 produces a B-mode image, and the data storage section 5 stores the B-mode image as a current image.

At Step S3, the correlation calculating section 6C calculates a correlation value between the initial image and current image.

At Step S4, the low-MI scan control section 6L goes back to Step S2 if the correlation value is not smaller than a threshold, and goes to Step S5 if the correlation value is smaller than the threshold.

Figure 4B:
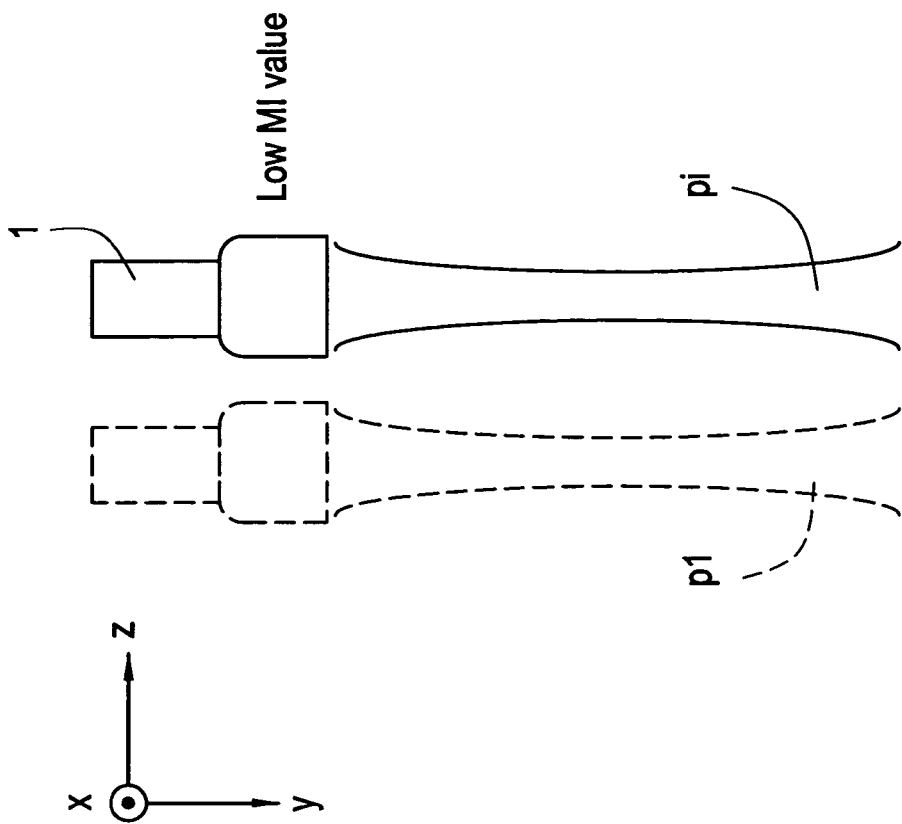
FIG. 4 is an explanatory diagram showing the position of scan planes corresponding the initial image and a current image.
Figure 4A:
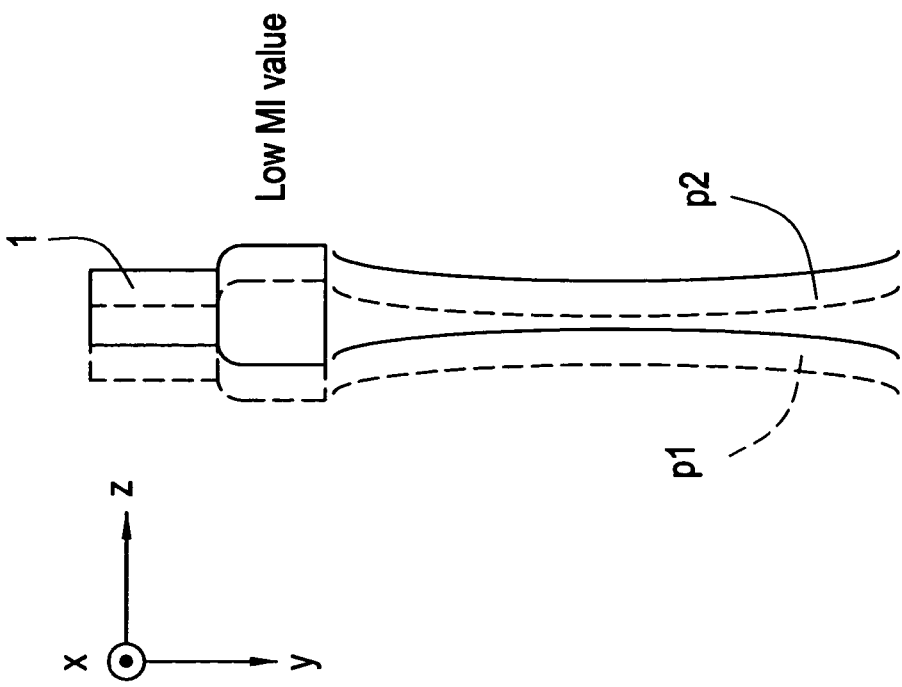

As shown in FIG. 4(a), when the position of the scan plane p1 corresponding to the initial image and that of a scan plane p2 corresponding to the current image are close to each other, the correlation value is not smaller than the threshold, and the process goes back to Step S2.

As shown in FIG. 4(b), when the position of the scan plane p1 corresponding to the initial image and that of a scan plane p1 corresponding to the current image are properly separated, the correlation value is smaller than the threshold, and the process goes to Step S5.

At Step S5, the high-MI scan control section 6H conducts a B-mode, CFM or PDI scan with such a high MI value as to break contrast agent, the image producing section 3 produces a B-mode, CFM or PDI image, and the data storage section 5 stores the B-mode, CFM or PDI image as original data for contrast-enhanced three-dimensional data.

Figure 5:
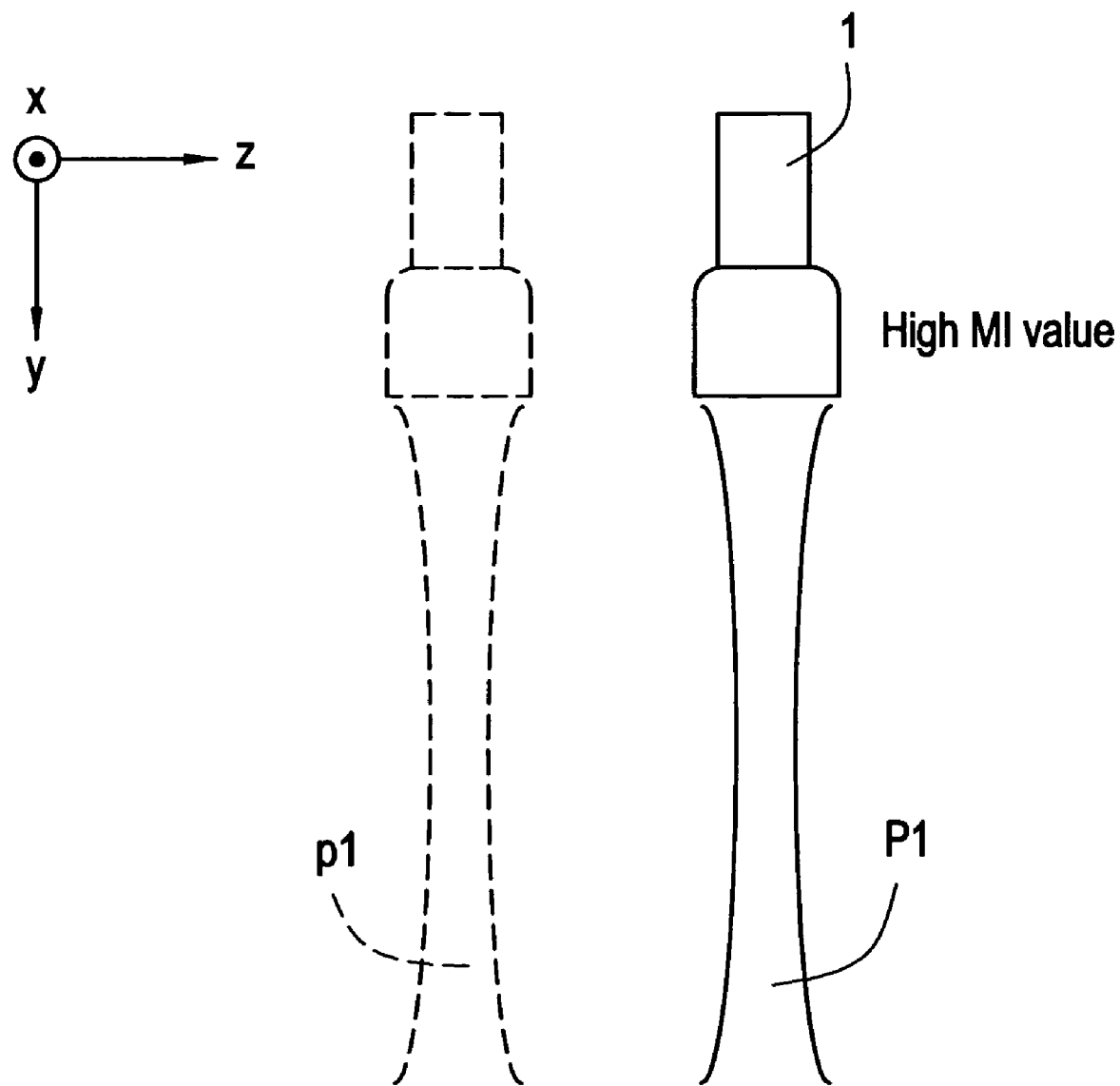
FIG. 5 is an explanatory diagram showing the position of a scan plane scanned with a high MI value.

FIG. 5 shows the position of a scan plane p1 scanned with a high MI value.

At Step S11, if a command to terminate acquisition is not issued, the control section 6 instructs the data storage section 5 to store an image that will be produced by a next scan by the low-MI scan control section 6L as a current image, and goes back to Step S1. If a command to terminate acquisition is issued, the process is terminated.

Figure 6:
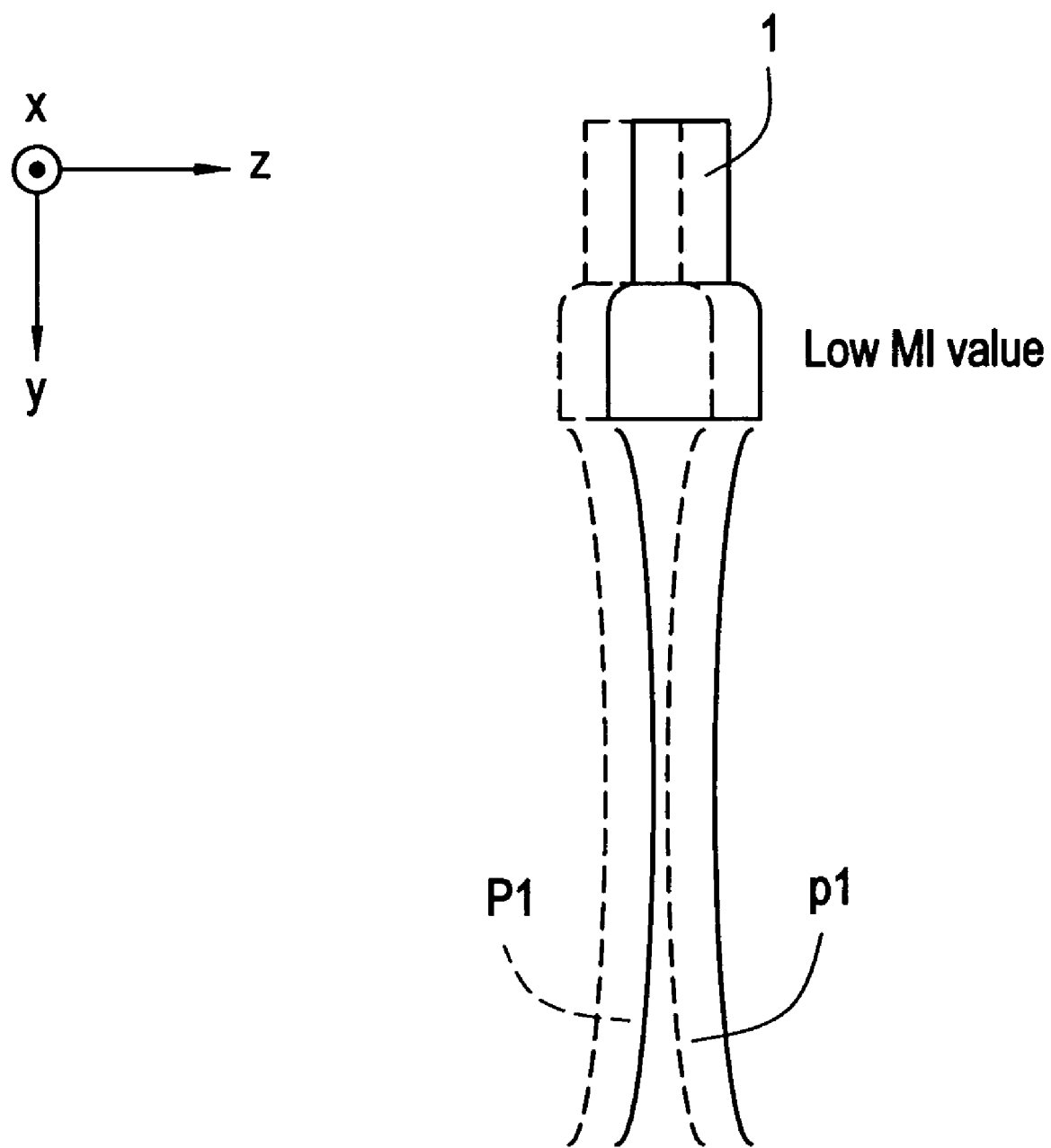
FIG. 6 is an explanatory diagram showing the position of a scan plane corresponding a new initial image.

FIG. 6 shows the position of a scan plane p1 corresponding a new initial image after going back to Step S1.

Figure 7:
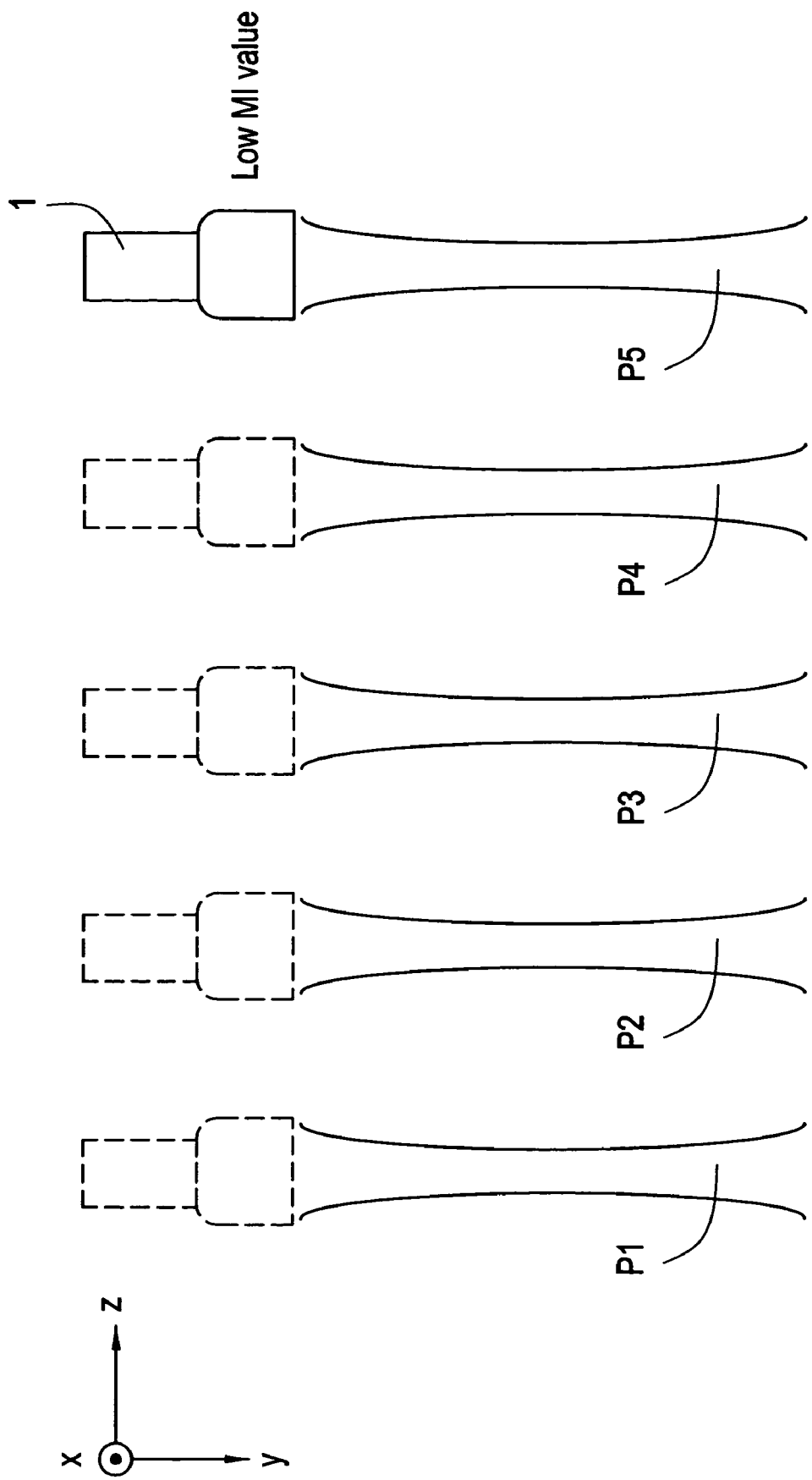
FIG. 7 is an explanatory diagram showing the distance for scan planes scanned with a high MI value.

As a result of the process, a high-MI scan can be conducted for scan planes P1, P2, P3, . . . at appropriate distances even for a different moving rate of the ultrasonic probe 1 or for a different subject or imaged region, as shown in FIG. 7.

Figure 8:
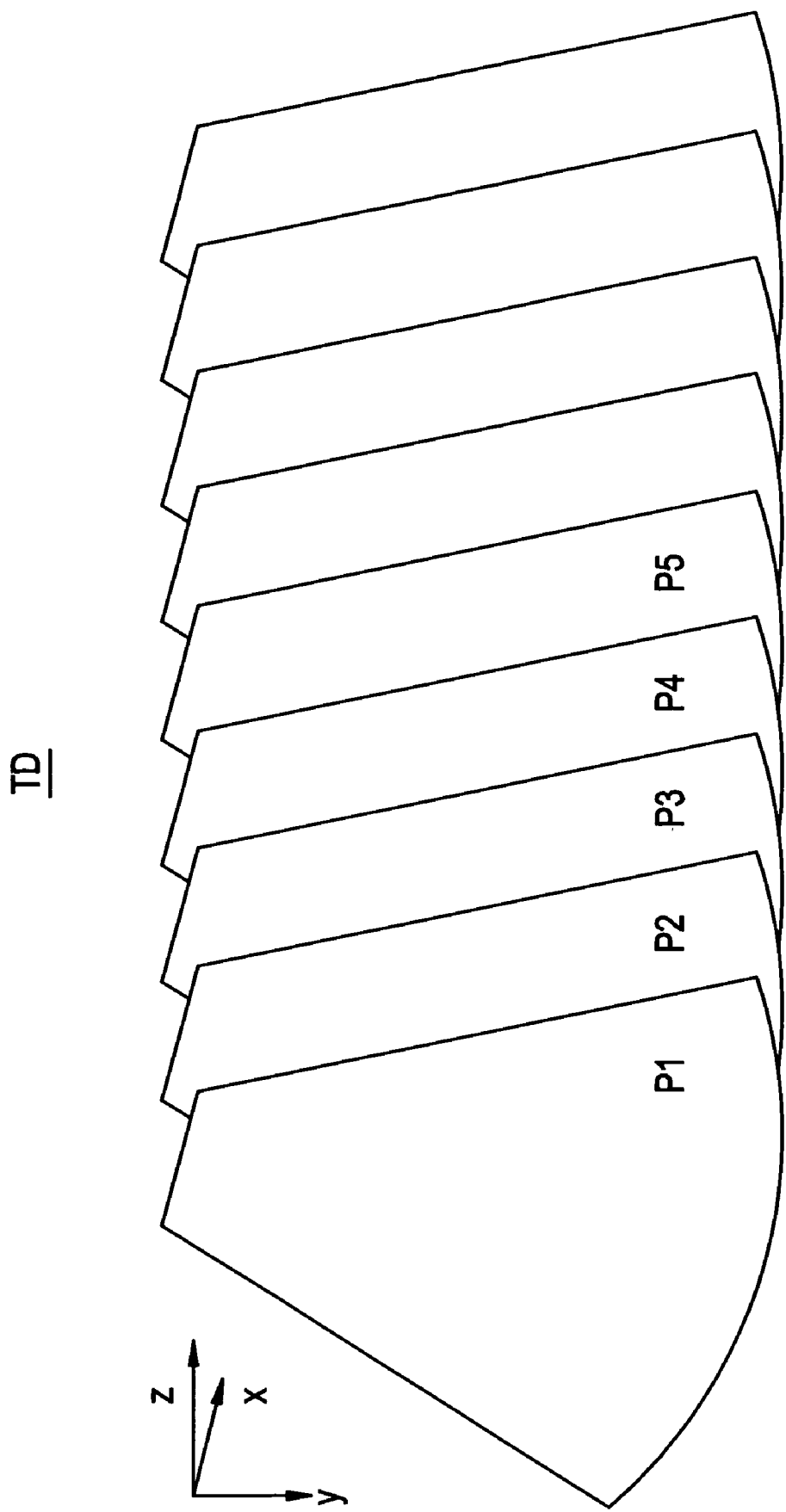
FIG. 8 is a conceptual diagram showing contrast-enhanced three-dimensional data.

Thus, the data storage section 5 can suitably acquire contrast-enhanced three-dimensional data TD as shown in FIG. 8.

Moreover, the distance between the scan planes P1, P2, P3, . . . (i.e., the density of the contrast-enhanced three-dimensional data TD in a direction orthogonal to a scan plane) can be adjusted by modifying the threshold.

Second Embodiment

Figure 9:
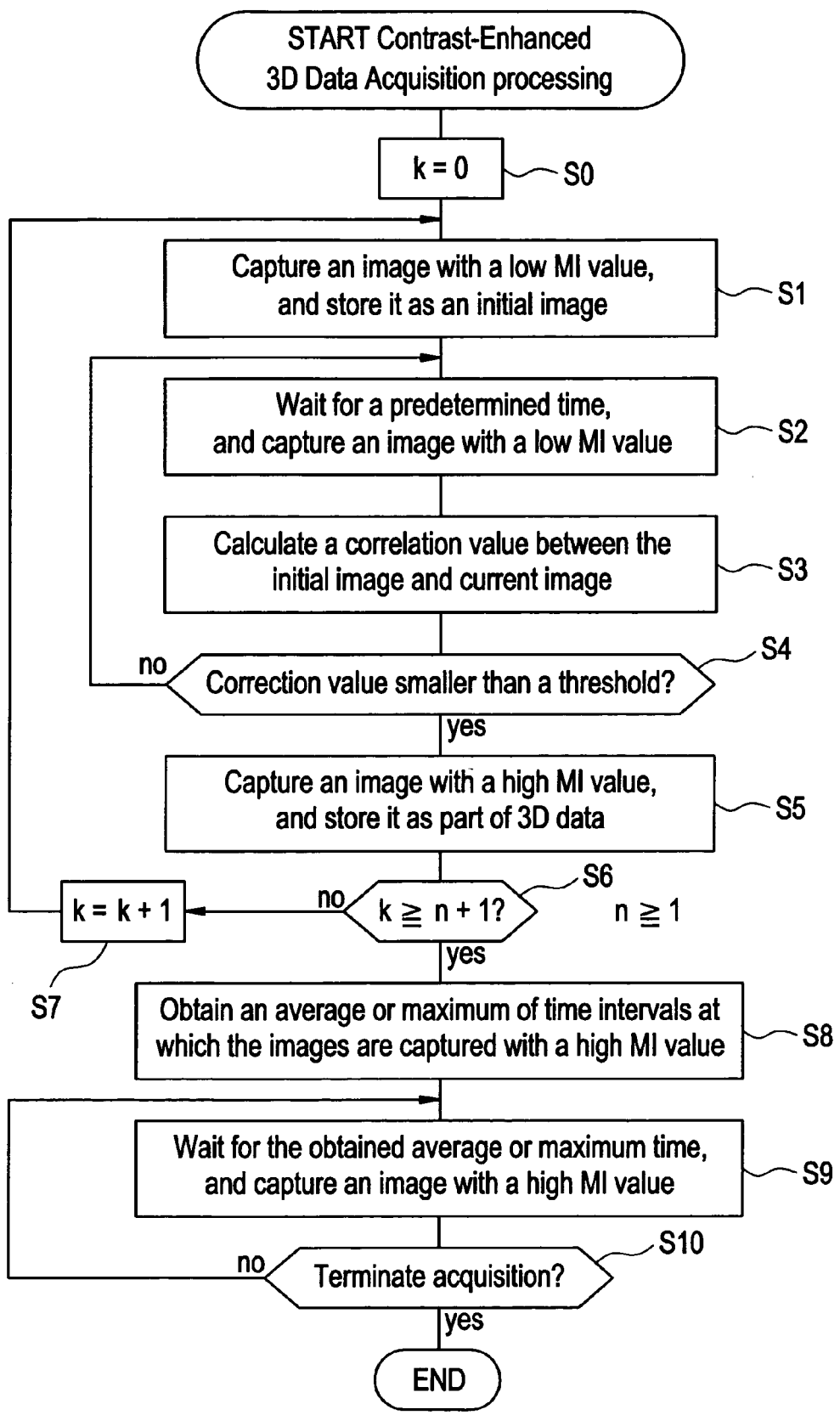
FIG. 9 is a flow chart showing contrast-enhanced three-dimensional data acquisition processing by the ultrasonic diagnostic apparatus in accordance with a Second Embodiment.

FIG. 9 is a flow chart showing a second example of contrast-enhanced three-dimensional data acquisition processing by the ultrasonic diagnostic apparatus 100.

The number of repetitions n ($\geq 1$) used in this processing is specified beforehand by the operator.

At Step S0, the control section 6 initializes a repetition counter k=0.

Steps S1-S5 are similar to those described in the First Embodiment.

At Step S6, the control section 6 goes to Step S7 if k$\geq$n+1 does not hold, and to Step S8 if k$\geq$n+1 holds.

At Step S7, the control section 6 increments the repetition counter k. The process then goes back to Step S1.

At Step S8, the control section 6 obtains an average (or maximum) of time intervals at which images are captured with a high MI value. If n=1 has been specified, only one time interval is acquired, and it is used as the average (and maximum).

At Step S10, the high-MI scan control section 6H conducts a B-mode, CFM or PDI scan with a high MI value at the average (or maximum) time interval acquired at Step S8, the image producing section 3 produces a B-mode, CFM or PDI image, and the data storage section 5 stores the B-mode, CFM or PDI image as original data for contrast-enhanced three-dimensional data.

At Step S11, if a command to terminate acquisition is not issued, the control section 6 goes back to Step S10. If a command to terminate acquisition is issued, the process is terminated.

As a result of the process, contrast-enhanced three-dimensional data can be suitably acquired even for a different moving rate of the ultrasonic probe 1 or for a different subject or imaged region because a high-MI scan is conducted at an appropriate scan plane distance. Moreover, since the correlation calculation is conducted only for first n times, processing load is mitigated.

Third Embodiment

Figure 10:
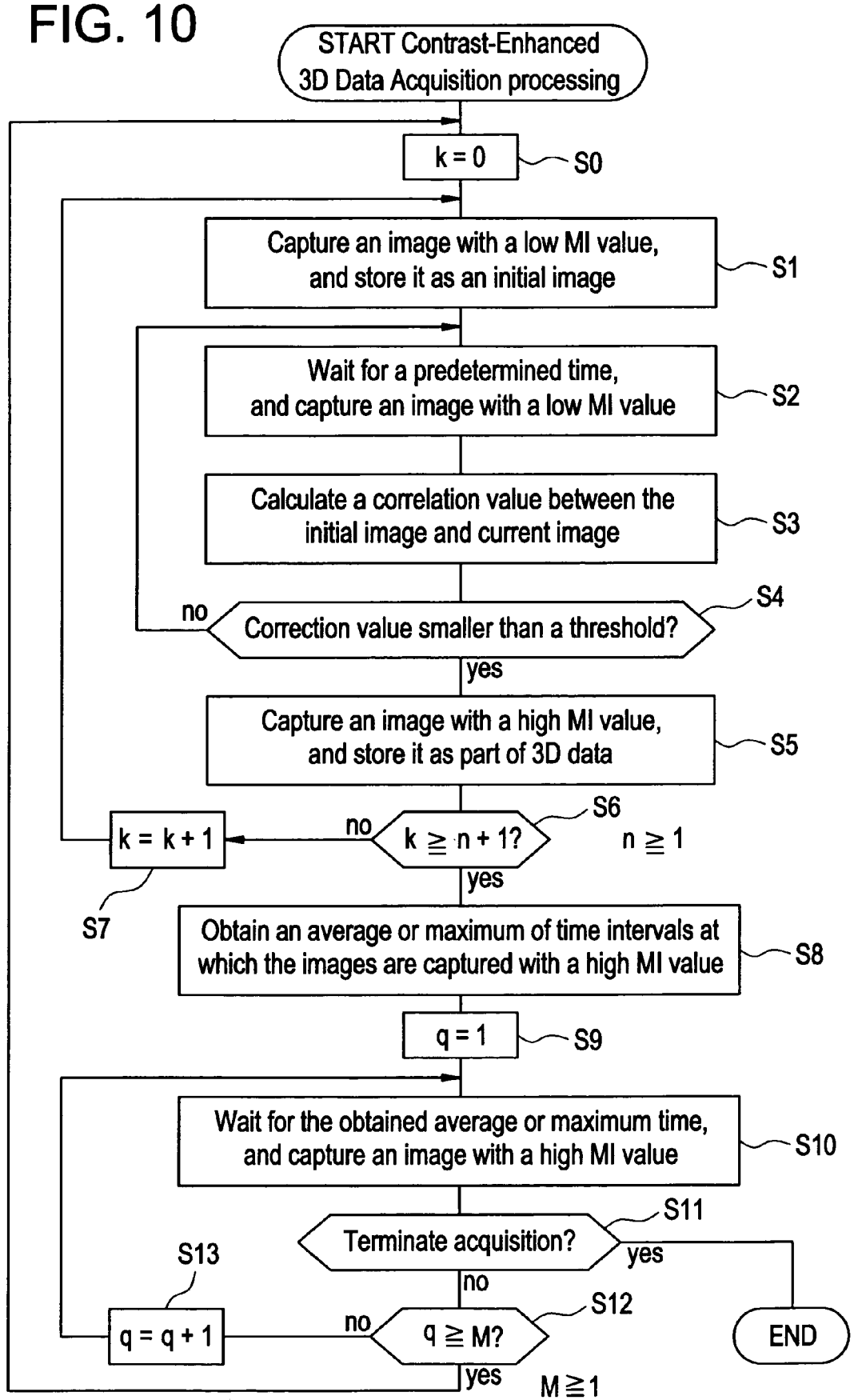
FIG. 10 is a flow chart showing contrast-enhanced three-dimensional data acquisition processing by the ultrasonic diagnostic apparatus in accordance with a Third Embodiment.

FIG. 10 is a flow chart showing a third example of contrast-enhanced three-dimensional data acquisition processing by the ultrasonic diagnostic apparatus 100.

The numbers of repetitions n ($\geq$1) and M ($\geq$1) used in this processing are specified beforehand by the operator.

Steps S0-S8 are similar to those described in the Second Embodiment.

At Step S9, the control section 6 initializes a repetition counter q=1.

At Step S10, the high-MI scan control section 6H conducts a B-mode, CFM or PDI scan with a high MI value at the average (or maximum) time interval acquired at Step S8, the image producing section 3 produces a B-mode, CFM or PDI image, and the data storage section 5 stores the B-mode, CFM or PDI image as original data for contrast-enhanced three-dimensional data.

At Step S11, if a command to terminate acquisition is not issued, the control section 6 goes to Step S12. If a command to terminate acquisition is issued, the process is terminated.

At Step S12, the control section 6 goes to Step S13 if q$\geq$M does not hold, and goes back to Step S0 if q$\geq$M holds.

At Step S13, the control section 6 increments the repetition counter q. The process then goes back to Step S10.

As a result of the process, contrast-enhanced three-dimensional data can be suitably acquired even for a different moving rate of the ultrasonic probe 1 or for a different subject or imaged region because a high-MI scan is conducted at an appropriate scan plane distance. Moreover, since the correlation calculation is not conducted while M scans are conducted with a high MI value, processing load is mitigated. Furthermore, the process goes back to processing for conducting image capture with a low MI value and calculating a correlation value after the M scans with a high MI value, and therefore, the time interval may be properly corrected in the course of acquisition of three-dimensional data.

Fourth Embodiment

Figure 11:
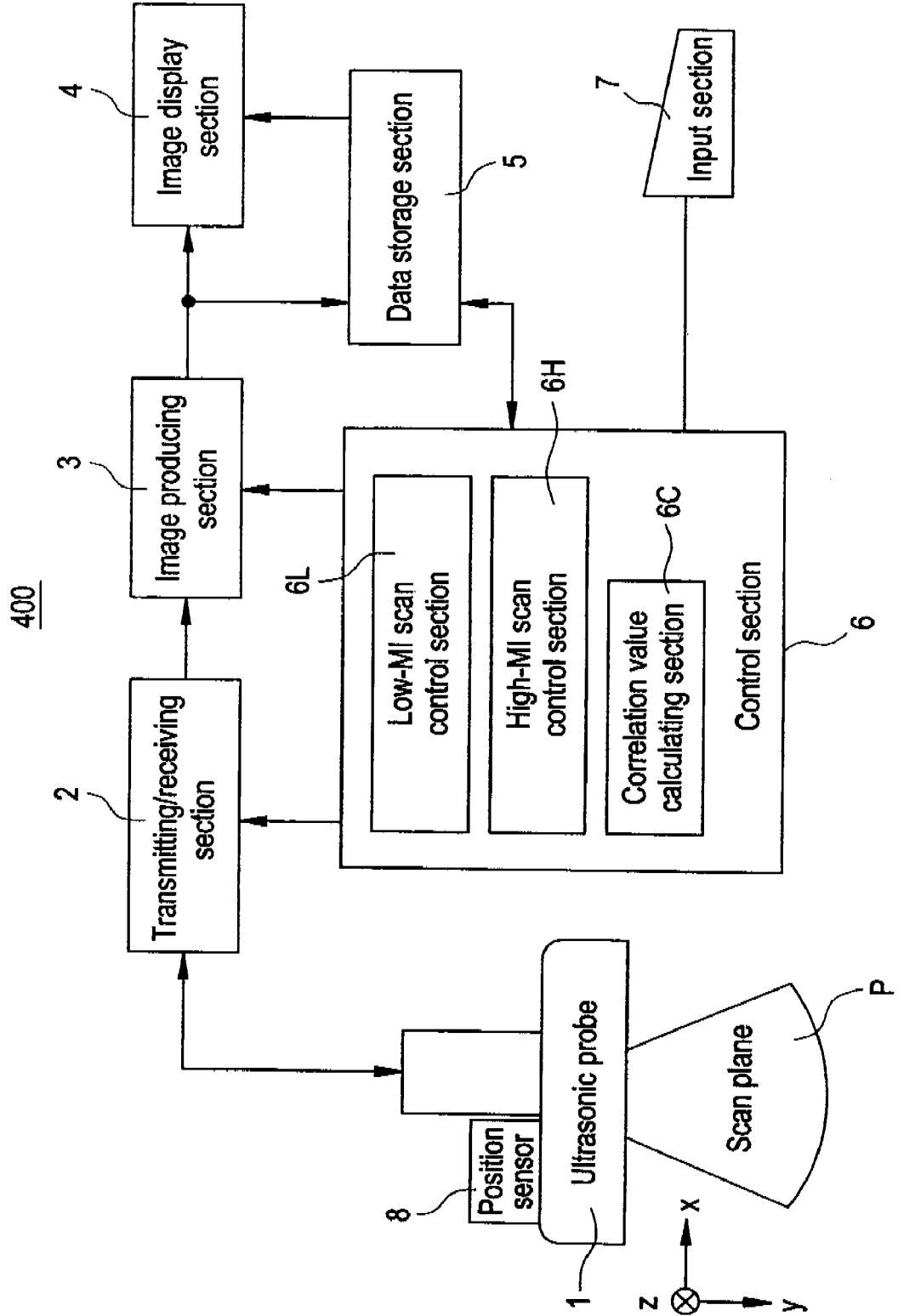
FIG. 11 is a configuration diagram showing an ultrasonic diagnostic apparatus in accordance with a Fourth Embodiment.

FIG. 11 is a configuration diagram showing an ultrasonic diagnostic apparatus in accordance with a Fourth Embodiment.

The ultrasonic diagnostic apparatus 400 is basically the same as the ultrasonic diagnostic apparatus 100 in accordance with the First Embodiment except that the ultrasonic probe 1 is provided with a position sensor 8.

Figure 12:
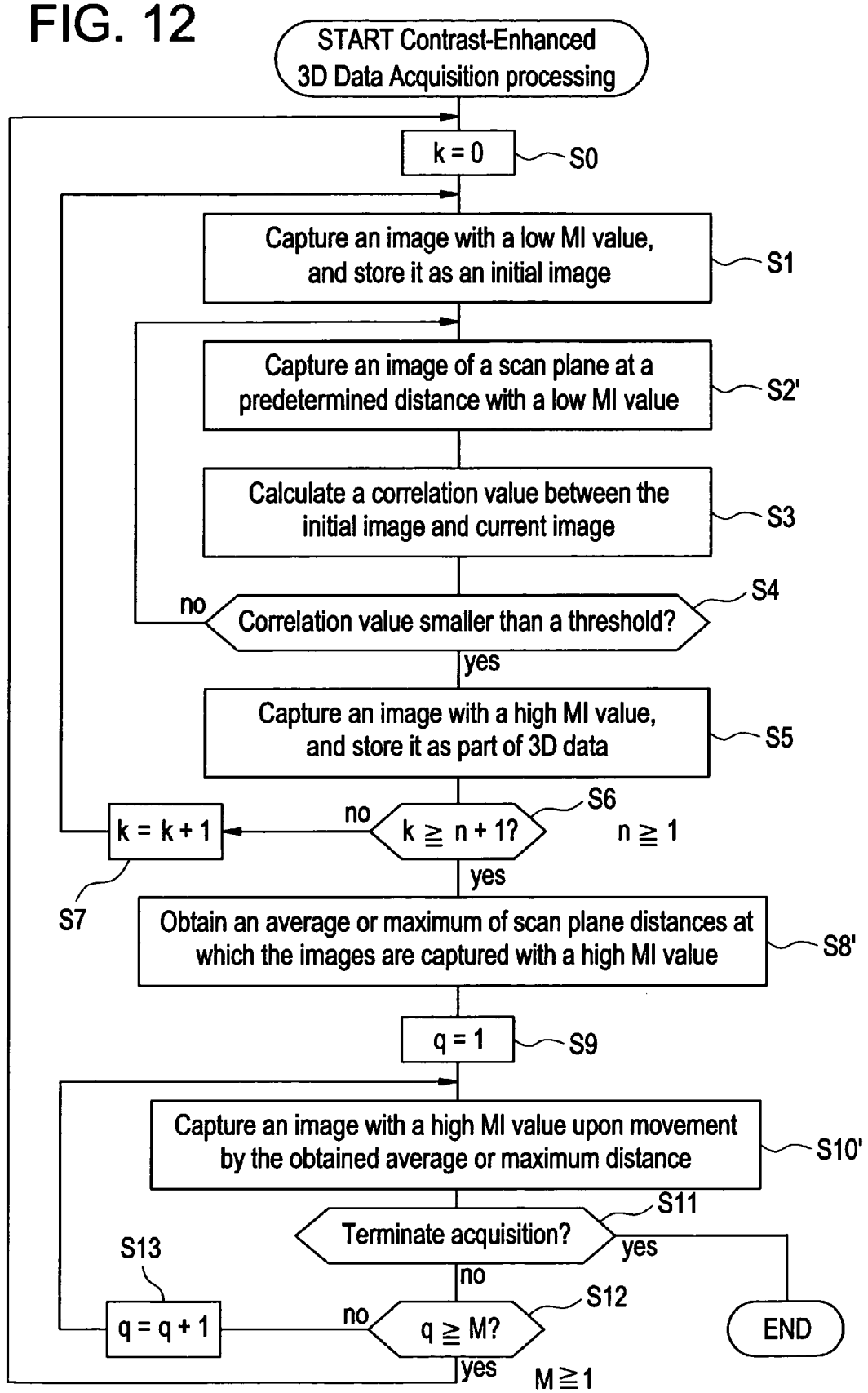
FIG. 12 is a flow chart showing contrast-enhanced three-dimensional data acquisition processing by the ultrasonic diagnostic apparatus in accordance with the Fourth Embodiment.

FIG. 12 is a flow chart showing contrast-enhanced three-dimensional data acquisition processing by the ultrasonic diagnostic apparatus 400.

At Step S0, the control section 6 initializes a repetition counter k=0.

At Step S1, the low-MI scan control section 6L conducts a B-mode scan with a low MI value, the image producing section 3 produces a B-mode image, and the data storage section 5 stores the B-mode image as an initial image.

FIG. 3 shows the position of a scan plane p1 corresponding to the initials image.

At Step S2', the low-MI scan control section 6L waits for the position sensor 8 to detect a predetermined distance from the previous scan plane and conducts a B-mode scan with a low MI value, the image producing section 3 produces a B-mode image, and the data storage section 5 stores the B-mode image as a current image.

At Step S3, the correlation calculating section 6C calculates a correlation value between the initial image and current image.

At Step S4, the low-MI scan control section 6L goes back to Step S2' if the correlation value is not smaller than a threshold, and goes to Step S5 if the correlation value is smaller than the threshold.

At Step S5, the high-MI scan control section 6H conducts a B-mode, CFM or PDI scan with a high MI value, the image producing section 3 produces a B-mode, CFM or PDI image, and the data storage section 5 stores the B-mode, CFM or PDI image as original data for contrast-enhanced three-dimensional data.

At Step S6, the control section 6 goes to Step S7 if k$\geq$n+1 does not hold, and to Step S8 if k$\geq$n+1 holds.

At Step S7, the control section 6 increments a repetition counter k. The process then goes back to Step S1.

At Step S8', the control section 6 obtains an average (or maximum) of scan plane distances at which images are captured with a high MI value. If n=1 has been specified, only one scan plane distance is acquired, and it is used as the average (and maximum).

At Step S9, the control section 6 initializes a repetition counter to q=1.

At Step S10', the high-MI scan control section 6H conducts a B-mode, CFM or PDI scan with a high MI value at the average (or maximum) time interval acquired at Step S8', the image producing section 3 produces a B-mode, CFM or PDI image, and the data storage section 5 stores the B-mode, CFM or PDI image as original data for contrast-enhanced three-dimensional data.

At Step S10', if a command to terminate acquisition is not issued, the control section 6 goes to Step S12. If a command to terminate acquisition is issued, the process is terminated.

At Step S12, the control section 6 goes to Step S13 if q$\geq$M does not hold, and goes back to Step S0 if q$\geq$M holds.

At Step S13, the control section 6 increments the repetition counter q. The process then goes back to Step S10'.

As a result of the process, contrast-enhanced three-dimensional data can be suitably acquired even for a different moving rate of the ultrasonic probe 1 or for a different subject or imaged region because a high-MI scan is conducted at an appropriate scan plane distance.

Although FIG. 12 is depicted corresponding to FIG. 10, it can be easily modified to correspond to FIG. 2 or 9.

Fifth Embodiment

Figure 13:
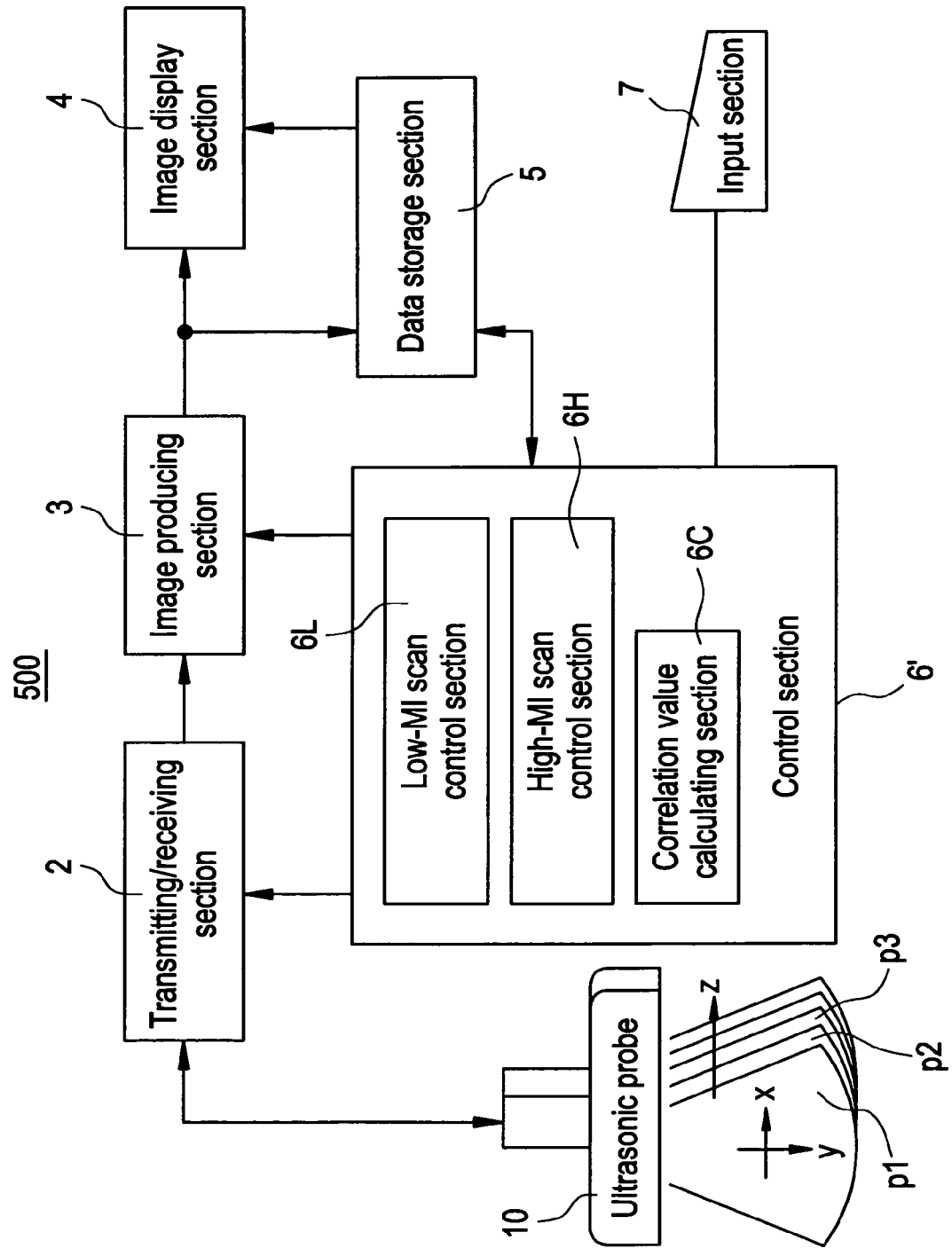
FIG. 13 is a configuration diagram showing an ultrasonic diagnostic apparatus in accordance with a Fifth Embodiment.

FIG. 13 is a configuration diagram showing an ultrasonic diagnostic apparatus in accordance with a Fifth Embodiment.

The ultrasonic diagnostic apparatus 500 is basically the same as the ultrasonic diagnostic apparatus 100 in accordance with the First Embodiment except that it comprises a two-dimensional array ultrasonic probe 10, and a control section 6' that can change the position of a scan plane by electronically moving a scan plane like a flap in a direction orthogonal to a scan plane.

Figure 14:
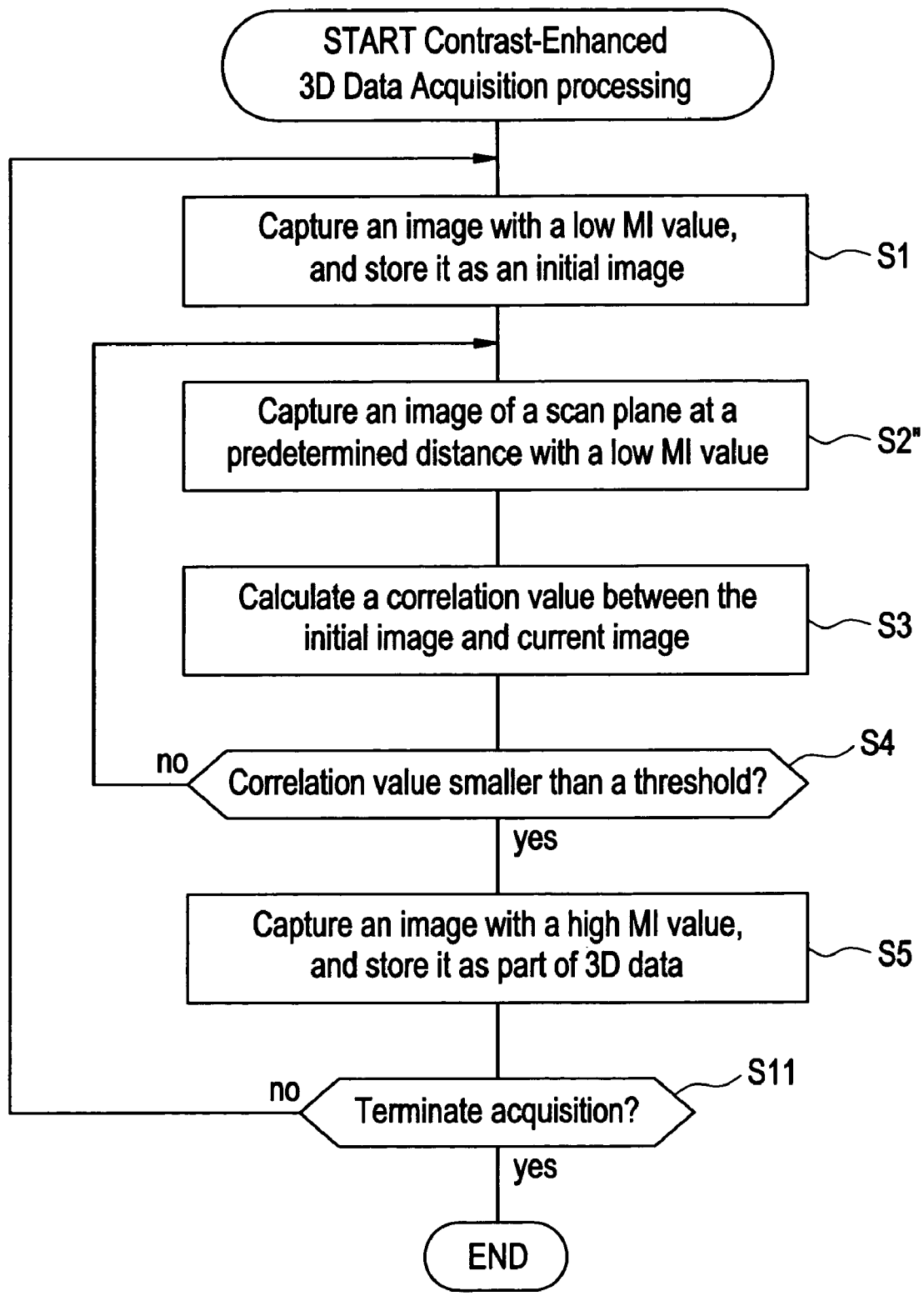
FIG. 14 is a flow chart showing contrast-enhanced three-dimensional data acquisition processing by the ultrasonic diagnostic apparatus in accordance with the Fifth Embodiment.

FIG. 14 is a flow chart showing contrast-enhanced three-dimensional data acquisition processing by the ultrasonic diagnostic apparatus 500.

The operator injects contrast agent into a subject, puts the ultrasonic probe 10 against the subject, activates the contrast-enhanced three-dimensional data acquisition processing, and then, electronically moves a scan plane (x-y plane) of the ultrasonic probe 10 in an orthogonal direction (z-direction) at a predetermined angular distance.

At Step S1, the low-MI scan control section 6L conducts a B-mode scan with a low MI value, the image producing section 3 produces a B-mode image, and the data storage section 5 stores the B-mode image as an initial image.

Figure 15:
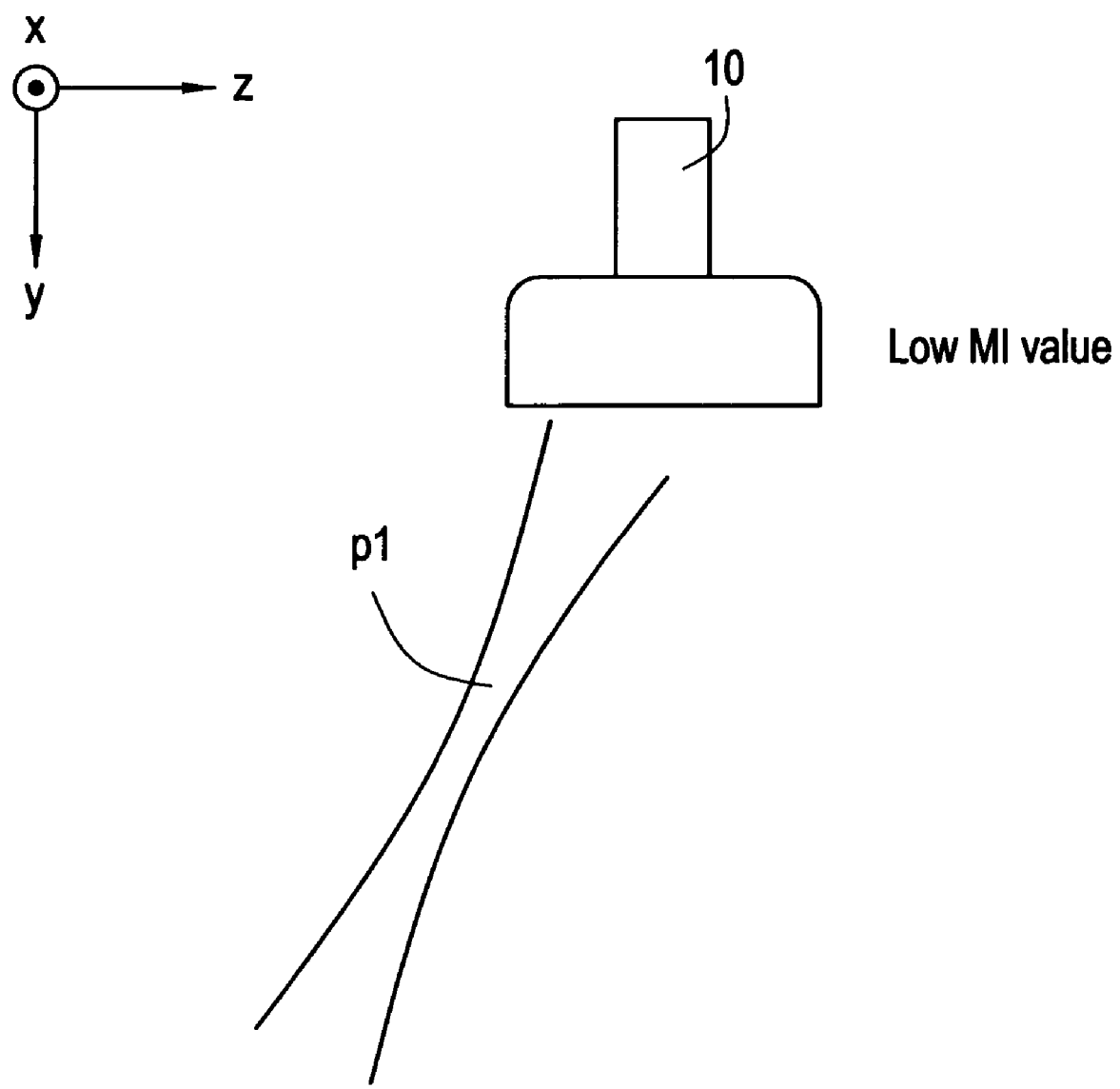
FIG. 15 is an explanatory diagram showing the position of a scan plane corresponding an initial image.

FIG. 15 shows the position of a scan plane p1 corresponding to the initial image.

At Step S2", the low-MI scan control section 6L changes the scan plane to one lying at a predetermined distance from the previous one and conducts a B-mode scan with a low MI value, the image producing section 3 produces a B-mode image, and the data storage section 5 stores the B-mode image as a current image.

At Step S3, the correlation calculating section 6C calculates a correlation value between the initial image and current image.

At Step S4, the low-MI scan control section 6L goes back to Step S2" if the correlation value is not smaller than a threshold, and goes to Step S5 if the correlation value is smaller than the threshold.

As shown in FIG. 16(*a*), when the position of the scan plane p1 corresponding to the initial image and that of a scan plane p2 corresponding to the current image are close to each other, the correlation value is not smaller than the threshold, and the process goes back to Step S2".

As shown in FIG. 16(*b*), when the position of the scan plane p1 corresponding to the initial image and that of a scan plane p1 corresponding to the current image are properly separated, the correlation value is smaller than the threshold, and the process goes to Step S5.

At Step S5, the high-MI scan control section 6H conducts a B-mode, CFM or PDI scan with a high MI value, the image producing section 3 produces a B-mode, CFM or PDI image, and the data storage section 5 stores the B-mode, CFM or PDI image as original data for contrast-enhanced three-dimensional data.

Figure 17:
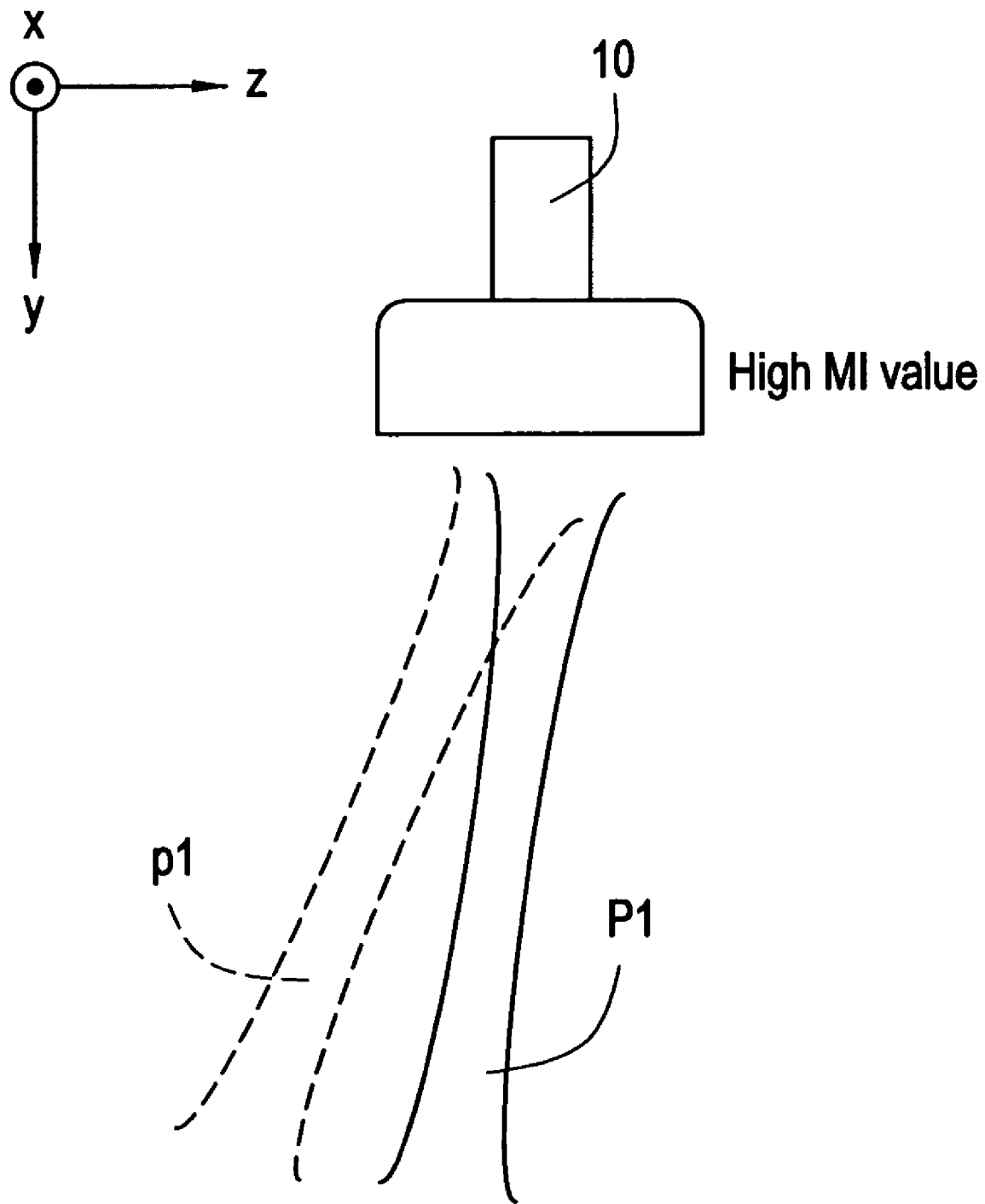
FIG. 17 is an explanatory diagram showing the position of a scan plane scanned with a high MI value.

FIG. 17 shows the position of a scan plane p1 scanned with a high MI value.

At Step S11, if a command to terminate acquisition is not issued, the control section 6 notices the data storage section 5 to store an image that will be produced by a next scan by the low-MI scan control section 6L as a current image, and goes back to Step S1. If a command to terminate acquisition is issued, the process is terminated.

Figure 18:
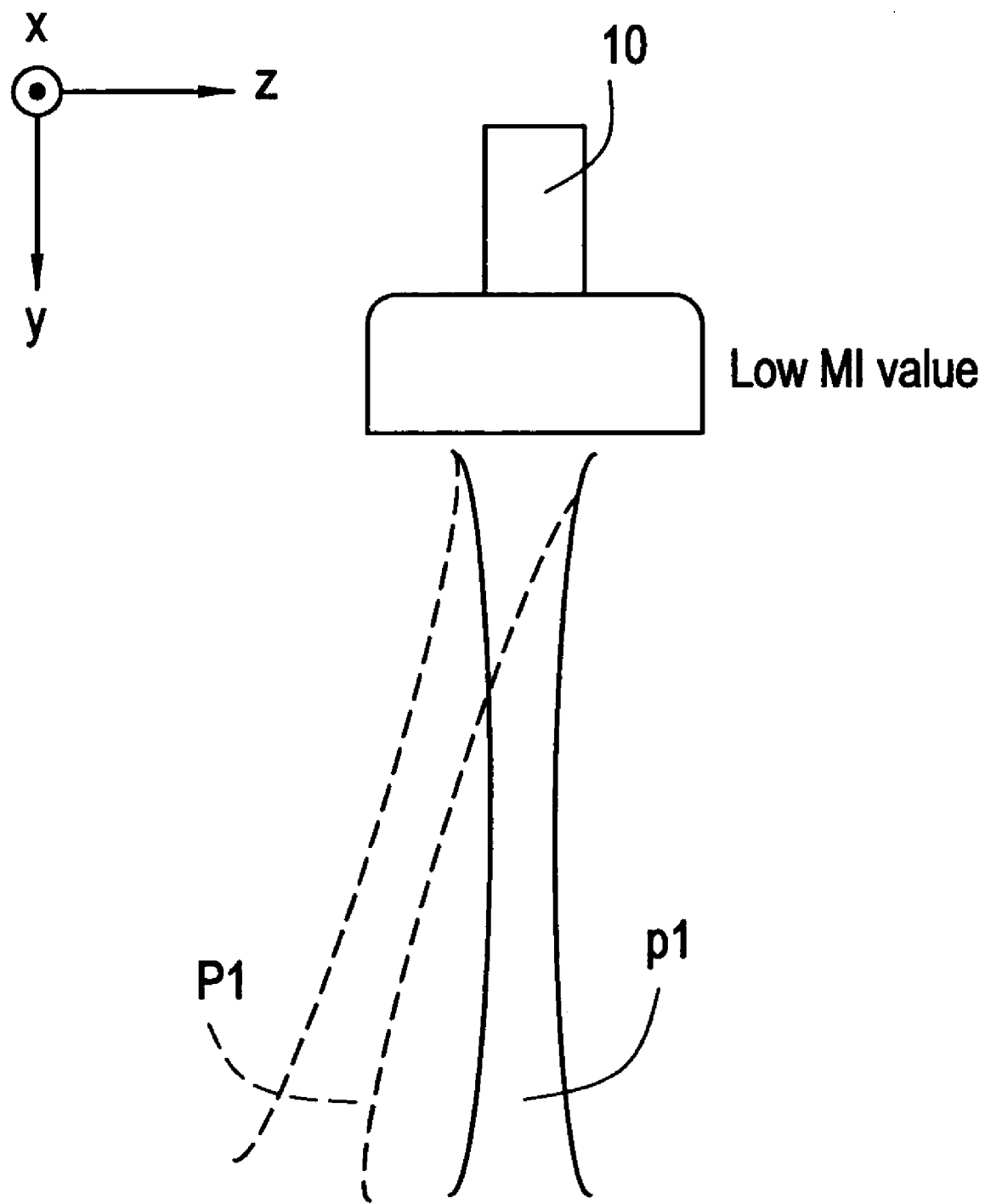
FIG. 18 is an explanatory diagram showing the position of a scan plane corresponding a new initial image.

FIG. 18 shows the position of a scan plane p1 corresponding a new initial image after going back to Step S1.

Figure 19:
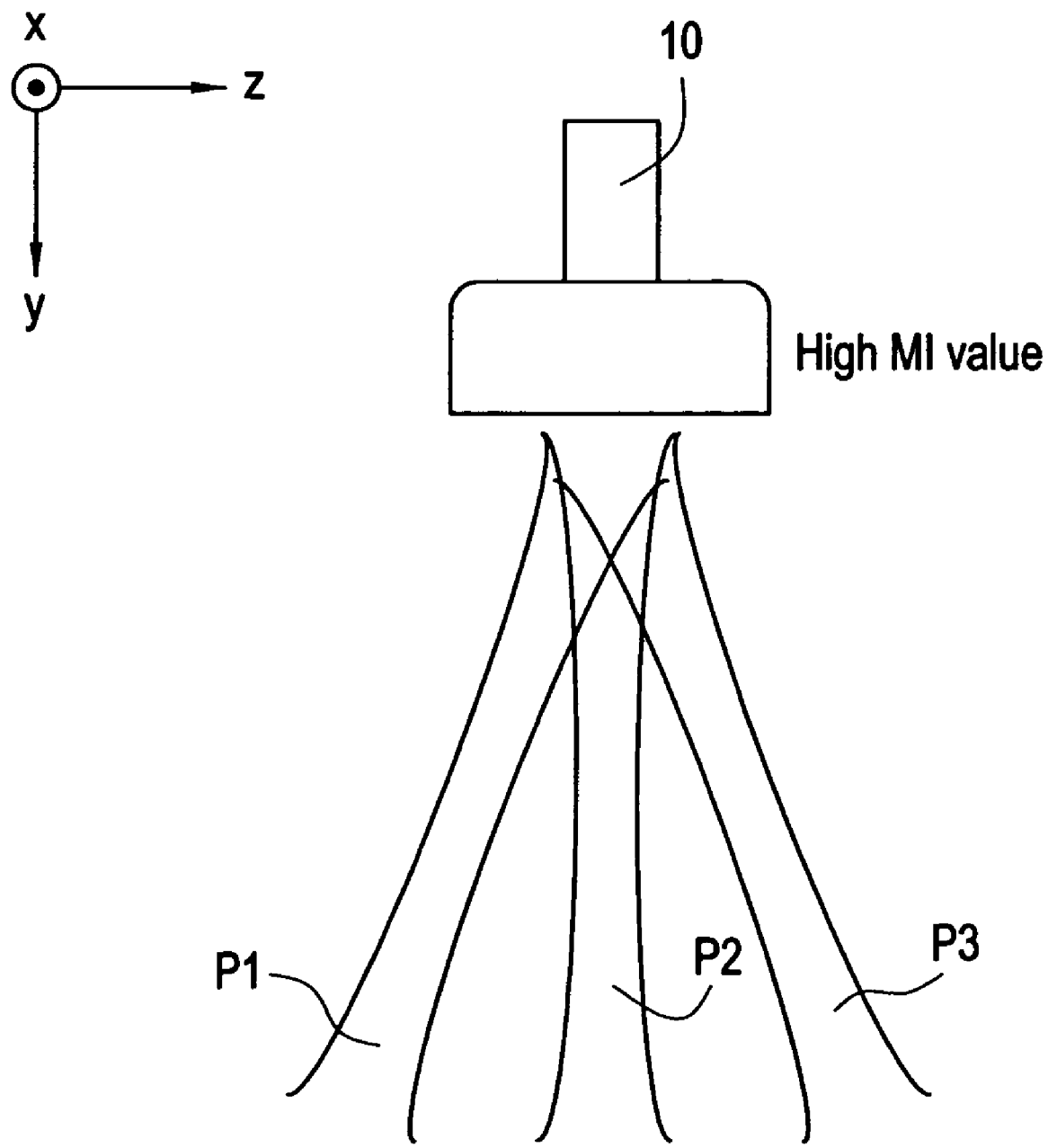
FIG. 19 is an explanatory diagram showing a distance for scan planes scanned with a high MI value.

As a result of the process, a high-MI scan can be conducted for scan planes P1, P2, . . . at appropriate distances even for a different subject or imaged region, as shown in FIG. 19.

Figure 20:
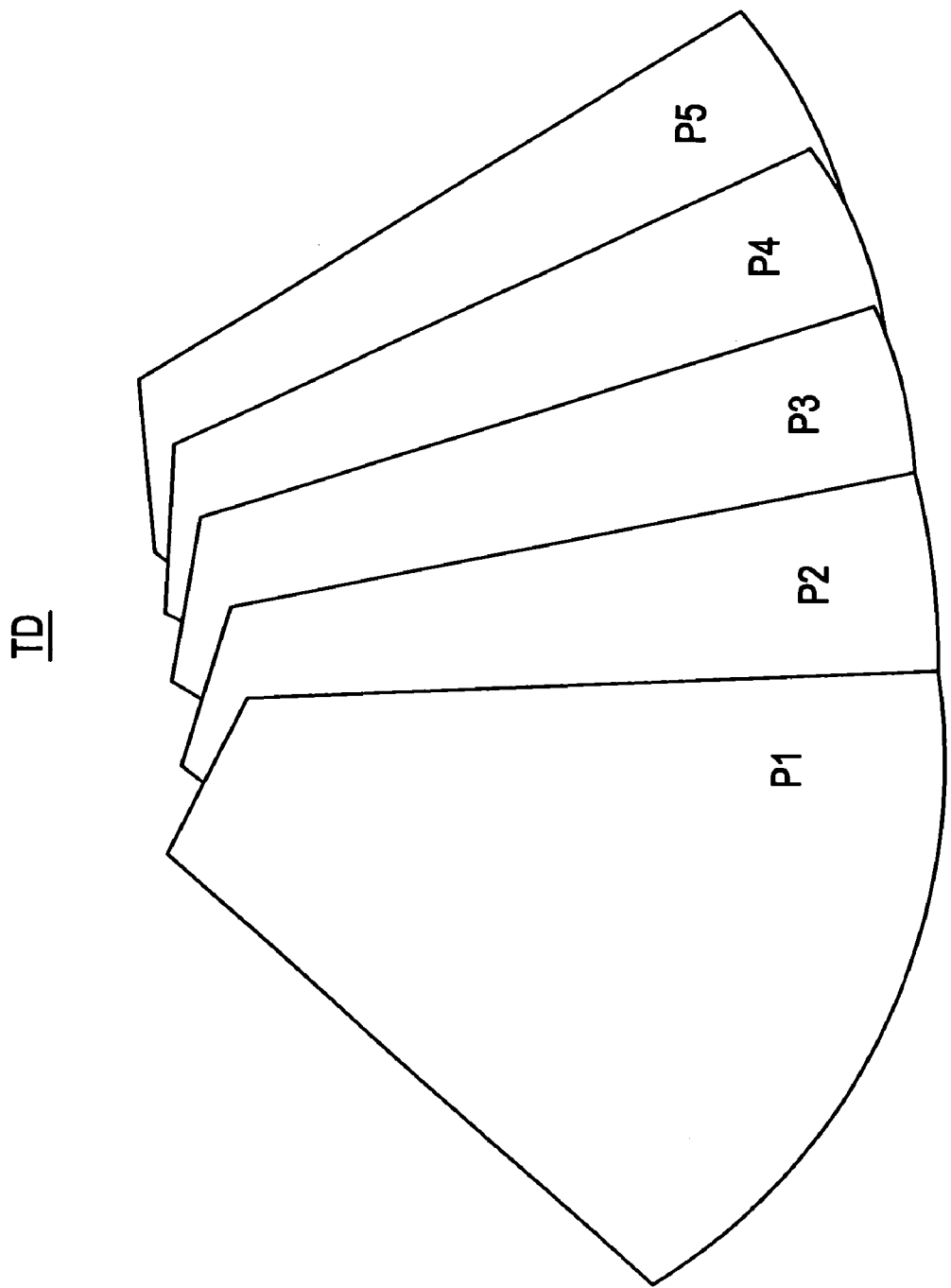
FIG. 20 is a conceptual diagram showing contrast-enhanced three-dimensional data.

Thus, the data storage section 5 can suitably acquire contrast-enhanced three-dimensional data TD as shown in FIG. 20.

Moreover, the distance between the scan planes P1, P2, . . . (i.e., the density of the contrast-enhanced three-dimensional data TD in a direction orthogonal to the scan plane) can be adjusted by modifying the threshold.

Although FIG. 14 is depicted corresponding to FIG. 2, it can be easily modified to correspond to FIG. 9, 10 or 12.

Another Embodiment

Although a case in which the operator moves the ultrasonic probe 1 in a direction orthogonal to the scan plane is assumed in the First-Fourth Embodiments, ultrasonic probe moving means for mechanically moving the ultrasonic probe 1 at a constant rate may be employed.

Many widely different embodiments of the invention may be configured without departing from the spirit and the scope of the present invention. It should be understood that the present invention is not limited to the specific embodiments described in the specification, except as defined in the appended claims.

The invention claimed is:

1. An ultrasonic diagnostic apparatus comprising:
   an ultrasonic probe;
   a transmitting/receiving device configured to drive said ultrasonic probe to scan a subject in a planar manner with an ultrasonic beam;
   a low-mechanical index (MI) scan control device configured to repeatedly conduct a scan with the ultrasonic beam at a level as not to break a contrast agent to obtain an initial image and a current image;
   an image producing device configured to produce a plurality of images, each image of the plurality of images based on received data obtained from one scan plane, the plurality of images including the initial image, the current image, and a contrast-enhanced image;
   a correlation value calculating device configured to calculate a correlation value between the initial image and the current image; and
   a high-MI scan control device configured to when the correlation value is less than a threshold value to capture the contrast-enhanced image with the ultrasonic beam at a level to break the contrast agent and also to return control to said low-MI scan control device.

2. The ultrasonic diagnostic apparatus of claim 1 further comprising an imaging scan time interval acquisition device configured to acquire a plurality of time intervals between a plurality of the contrast-enhanced threshold image captures conducted by said high-MI scan control device, wherein after conducting the plurality of contrast-enhanced image captures, said high-MI scan control device is configured to conduct an image capture of a plurality of interval image captures spaced by one of the acquired time intervals of the plurality of acquired time intervals with the ultrasonic beam at the level to break the contrast agent without returning control to said low-MI scan control device.

3. The ultrasonic diagnostic apparatus of claim 2, wherein said high-MI scan control device is configured to return control to said low-MI scan control device after conducting the plurality of interval image captures with the ultrasonic beam at the level to break the contrast agent for M times without returning control to said low-MI scan control device, wherein M is a number of repetitions of the plurality of interval image captures by said high-MI scan control device, and wherein M≧1.

4. The ultrasonic diagnostic apparatus of claim 1 further comprising an imaging scan time interval acquisition device configured to acquire a plurality of time intervals between a plurality of contrast-enhanced image captures conducted by said high-MI scan control device, wherein after acquiring N time intervals of the plurality of time intervals, said high-MI scan control device is configured to conduct an image capture of a plurality of interval image captures with the ultrasonic beam at the level to break the contrast agent at spaced by an average or a maximum of said acquired N time intervals without returning control to said low-MI scan control device, wherein N is a number of repetitions of the scan by said low-MI scan control device, and wherein N≧2.

5. The ultrasonic diagnostic apparatus of claim 4, wherein said high-MI scan control device is configured to return control to said low-MI scan control device after conducting the plurality of interval image captures with the ultrasonic beam at the level to break the contrast agent spaced by the average or the maximum of said acquired N time intervals for M times without returning control to said low-MI scan control device, wherein M is a number of repetitions of the plurality of interval image captures by said high-MI scan control device during the plurality of subsequent time intervals, and wherein M≧1.

6. The ultrasonic diagnostic apparatus of claim 1 further comprising an ultrasonic probe moving device configured to move said ultrasonic probe in a direction orthogonal to a scan plane at a constant rate.

7. The ultrasonic diagnostic apparatus of claim 1 wherein said low-MI scan control device and said high-MI scan control device are each configured to conduct a B-mode scan.

8. The ultrasonic diagnostic apparatus of claim 1 wherein said low-MI scan control device is configured to conduct a B-mode scan, and said high-MI scan control device is configured to conduct one of a CFM scan, a PDI scan, a harmonic imaging scan, and a contrast application scan.

9. The ultrasonic diagnostic apparatus of claim 1 further comprising an ultrasonic probe position detecting device configured to detect a position of said ultrasonic probe.

10. An ultrasonic diagnostic apparatus comprising:
an ultrasonic probe;
an ultrasonic probe position detecting device configured to detect a position of said ultrasonic probe;
a transmitting/receiving device configured to drive said ultrasonic probe to repeatedly scan a subject in a planar manner with an ultrasonic beam;
a low-mechanical index (MI) scan control device configured to repeatedly conduct a scan with the ultrasonic beam at a level as not to break a contrast agent to obtain an initial image and a current image;
an image producing device configured to produce a plurality of images, each image of the plurality of images based on received data obtained from one scan plane, the plurality of images including the initial image, the current image, and a contrast-enhanced image;
a correlation value calculating device configured to calculate a correlation value between the initial image and the current image;
a high-MI scan control device configured to when the correlation value is less than a threshold value to capture the contrast-enhanced image with the ultrasonic beam at a level to break the contrast agent and also to return control to said low-MI scan control device; and
an imaging scan plane distance acquisition device configured to acquire a plurality of distances between scan planes of a plurality of the contrast-enhanced image captures conducted by said high MI scan control device, the plurality of distances between scan planes acquired from said ultrasonic probe position detecting device;
wherein, said high-MI scan control device is configured to, after one acquisition of a first distance of the plurality of distances between scan planes, to conduct at least one interval image capture with the ultrasonic beam at the level to break the contrast agent spaced by said first distance without returning control to said low-MI scan control device.

11. The ultrasonic diagnostic apparatus of claim 10, wherein said high-MI scan control device is configured to return control to said low-MI scan control device after conducting the at least one interval image capture with the ultrasonic beam at the level to break the contrast agent at spaced by one of the acquired of distances between scan planes for M times without returning control to said low-MI scan control device, wherein M is a number of repetitions of the at least one interval image capture by said high-MI scan control device, and wherein M≧1.

12. The ultrasonic diagnostic apparatus of claim 10 further comprising an ultrasonic probe moving device configured to move said ultrasonic probe in a direction orthogonal to a scan plane at a constant rate.

13. The ultrasonic diagnostic apparatus of claim 10 wherein said low-MI scan control device and said high-MI scan control device are each configured to conduct a B-mode scan.

14. The ultrasonic diagnostic apparatus of claim 10 wherein said low-MI scan control device is configured to conduct a B-mode scan, and said high-MI scan control device is configured to conduct one of a CFM scan, a PDI scan, a harmonic imaging scan, and a contrast application scan.

15. An ultrasonic diagnostic apparatus comprising:
an ultrasonic probe;
an ultrasonic probe position detecting device configured to detect a position of said ultrasonic probe;
a transmitting/receiving device configured to drive said ultrasonic probe to repeatedly scan a subject in a planar manner with an ultrasonic beam;
a low-mechanical index (MI) scan control device configured to repeatedly conduct a scan with the ultrasonic beam at a level that does not break a contrast agent to obtain an initial image and a current image;
an image producing device configured to produce a plurality of images, each image of the plurality of images based on received data obtained from one scan plane, the plurality of images including the initial image, the current image, and a contrast-enhanced image;
a correlation value calculating device configured to calculate a correlation value between the initial image and the current image;
a high-MI scan control device configured to when the correlation value is less than a threshold value to capture the contrast-enhanced image with the ultrasonic beam at a level to break the contrast agent and also to return control to said low-MI scan control device; and
an imaging scan plane distance acquisition device configured to acquire a plurality of distances between scan planes, at each distance of the plurality of distances between scan planes and wherein said high-MI scan control device is configured to conduct at least one contrast-enhanced image capture, the plurality of distances between scan planes acquired from said ultrasonic probe position detecting device;
wherein after acquiring N distances of the plurality of distances between scan planes, said high-MI scan control device is configured to conduct at least one interval image capture with the ultrasonic beam at the level to break the contrast agent spaced by an average or a maximum of said N distances without returning control to said low-MI scan control device, wherein N is a number of repetitions of the scan by said low-MI scan control device, and wherein N≧2.

16. The ultrasonic diagnostic apparatus of claim 15, wherein said high-MI scan control device is configured to return control to said low-MI scan control device after conducting the at least one interval image capture with the ultrasonic beam at the level to break the contrast agent spaced by the average or the maximum of said N distances for a plurality of subsequent scan plane distances for M times without returning control to said low-MI scan control device, wherein M is a number of repetitions of the at least one interval image capture by said high-MI scan control device at the plurality of subsequent scan plane distances, and wherein $M \geq 1$.

17. The ultrasonic diagnostic apparatus of claim 15 further comprising an ultrasonic probe moving device configured to move said ultrasonic probe in a direction orthogonal to a scan plane at a constant rate.

18. The ultrasonic diagnostic apparatus of claim 15 wherein said low-MI scan control device and said high-MI scan control device are each configured to conduct a B-mode scan.

19. The ultrasonic diagnostic apparatus of claim 15 wherein said low-MI scan control device is configured to conduct a B-mode scan, and said high-MI scan control device is configured to conduct one of a CFM scan, a PDI scan, a harmonic imaging scan, and a contrast application scan.

* * * * *